United States Patent [19]
Burnier et al.

[11] Patent Number: 5,493,007
[45] Date of Patent: Feb. 20, 1996

[54] PLATELET AGGREGATION INHIBITORS HAVING HIGH SPECIFICITY FOR GPIIBIIIA

[75] Inventors: John P. Burnier, Pacifica; Thomas Gadek, Oakland; Robert S. McDowell, San Francisco, all of Calif.

[73] Assignee: Genentech, Inc., South San Francisco, Calif.

[21] Appl. No.: 311,835

[22] Filed: Sep. 23, 1994

Related U.S. Application Data

[63] Continuation of Ser. No. 173,716, Dec. 23, 1993, abandoned, which is a continuation of Ser. No. 45,566, Apr. 9, 1993, abandoned, which is a continuation of Ser. No. 681,802, Apr. 5, 1991, abandoned.

[51] Int. Cl.$^6$ .............................. C07K 5/00; C07K 7/00; C07K 17/00
[52] U.S. Cl. .................. 530/317; 530/329; 530/330; 930/270
[58] Field of Search ...................... 514/11–18; 530/317, 530/324–331; 930/270

[56] References Cited

U.S. PATENT DOCUMENTS

| | | |
|---|---|---|
| 4,517,686 | 5/1985 | Ruoslahti et al. . |
| 4,578,079 | 3/1986 | Ruoslahti et al. . |
| 4,589,881 | 5/1986 | Pierschbacher et al. . |
| 4,614,517 | 9/1986 | Ruoslahti et al. . |
| 4,661,111 | 4/1987 | Ruoslahti et al. . |

(List continued on next page.)

FOREIGN PATENT DOCUMENTS

| | | |
|---|---|---|
| 0275748 | 7/1988 | European Pat. Off. ............... 580/317 |
| 317053 | 5/1989 | European Pat. Off. . |
| 338634 | 10/1989 | European Pat. Off. . |
| 368486 | 5/1990 | European Pat. Off. . |
| 341915 | 11/1991 | European Pat. Off. . |
| 3841753A1 | 6/1990 | Germany . |
| 2207922 | 2/1989 | United Kingdom . |
| WO89/00200 | 1/1989 | WIPO . |
| WO89/04837 | 6/1989 | WIPO . |
| WO89/05150 | 6/1989 | WIPO . |
| WO89/07609 | 8/1989 | WIPO . |
| WO90/00178 | 1/1990 | WIPO . |
| WO90/06943 | 6/1990 | WIPO . |
| WO90/15620 | 12/1990 | WIPO . |
| WO91/01331 | 2/1991 | WIPO . |
| WO91/15515 | 10/1991 | WIPO . |

OTHER PUBLICATIONS

Ruggeri et al., *Proc. Natl. Acad. Sci.*, 83: 5708–5712 (1986).
Bagdy et al, Thrombosis and Haemostasis vol. 67 pp. 325–330 (1992).
Ginsberg et al., *J. Biol. Chem.*, 260: 3931–3936 (1985).
Pierschbacher et al., *Proc. Natl. Acad. Sci.*, 81: 5985–5988 (1984).
Kloczewiak et al., *Biochemistry*, 23: 1767–1774 (1984).
Gartner, T. K. and Bennett, J. S., *J. Biol. Chem.*, 260: 11891–11894 (1985).
Kieffer, N. and Phillips, D. R., *Annu. Rev. Cell Biol.*, 36: 329–357 (1990).
Plow, et al., *Proc. Natl. Acad. Sci. USA*, 82: 8057–8061 (1985).
Pytela et al., *Cell*, 40: 191–198 (1985).
Pytela et al., *Proc. Natl. Acad Sci. USA*, 82: 5766–5770 (1985).
Pytela et al., *Science*, 231: 1559–1562 (1985).
Gardner et al., *Cell*, 42: 439–448 (1985).
Pierschbacher et al., *Nature*, 309: 30–33 (1984).
D'Souza et al., *J. Biol. Chem.*, 263: 3943–3951 (1988).
Parise et al., *J. Biol. Chem.*, 262: 12597–12602 (1987).
Toda et al., *J. Cell. Biol.*, 105: 3097–3104 (1987).
Singer et al., *J. Cell. Biol.*, 104: 573–584 (1987).
Lash et al., *Develop Biol.*, 123: 411–420 (1987).
Haskel et al., *Thromb. Res.*, 56: 687–695 (1989).
Haverstick et al., *Blood*, 66: 946–952 (1985).
Plow et al., *Blood*, 70: 110–115 (1987).
Ruoslahti et al., *J. Clin. Invest.*, 87: 1–5 (1991).
Ali et al., *Peptides Proc. 11th Amer. Peptide Symposium*, La Jolla, CA, Marshall & Rivier, eds. (Jul. 9–14, 1989).
Pierschbacher et al., *J. Biol. Chem.*, 262(36): 17294–17298 (1987).
Garsky et al., *Pro. Natl. Acad. Sci. USA*, 86: 4022–4026 (1989).
Dennis et al., *Pro. Natl. Acad. Sci. USA*, 87: 2471–2475 (1989).
Chao et al., *Pro. Natl. Acad. Sci. USA*, 86: 8050–8054 (1989).
Shebuski et al., *J. Biol. Chem.*, 264: 21550–21556 (1989).
Gan et al., *J. Biol. Chem.*, 263: 19827–19832 (1989).
Huang et al., *Biochemistry*, 28: 661–666 (1989).
Huang et al., *J. Biol. Chem.*, 262: 16157–1613 (1987).
Joubert, Francois J. & Taljaard, Nico, *Biochimica et Biophysica Acta*, 579: 228–233 (1979).
Spatola, A. F. and Krzysztof, D., *Tetrahedron*, 44(3): 821–833 (1988).
Gero, T. and Spatola, A. F., *Biochem. Biophys. Res. Comm.*, 120(3): 840–845 (1984).
Edwards, J. V. and Spatola, A. F., *Biochem. Biophys. Res. Comm.*, 136(2): 730–736 (1986).
Spatola, A. F. and Edwards, J. V., *Biopolymers*, 25: s229–s244 (1986).
Davies et al., *Biochem Soc. Trans.*, 18: 11326–11328 (1990).
Drickamer et al., *J. Biol. Chem.*, 261: 6878–6887 (1986).
Rauvala et al., *J. Cell Biol.*, 107: 2293–2305 (1988).
Maes et al., *Fed. Europ. Biochem. Soc.*, 241: 41–45 (1988).
Moos et al., *Nature*, 334: 701–703 (1988).
Neurath et al., *Mol. Immun.*, 27: 539–549 (1990).
Kirchofer et al., *J. Biol. Chem.*, 265: 18525–18530 (1990).
Ratner et al., *Nature*, 313: 277–284 (1985).
Bond et al., *Biochemistry*, 28: 6110–6113 (1989).

*Primary Examiner*—Jill Warden
*Assistant Examiner*—Sheela J. Huff
*Attorney, Agent, or Firm*—Daryl B. Winter

[57] ABSTRACT

A peptide containing the tripeptide recognition sequences RGD or KGD in a cycle and an exocyclic group bearing a positive charge is provided. The compound is provided in therapeutic form for administration to a mammal and exhibits high specificity and potency as a platelet aggregation inhibitor without undesireable side effects.

4 Claims, No Drawings

U.S. PATENT DOCUMENTS 4,683,291  7/1987  Zimmerman et al. .
4,792,525  12/1988 Ruoslahti et al. .
4,857,508  8/1989  Adams et al. .
4,879,313  11/1989 Tjoeng et al. .
5,023,233  6/1991  Nutt et al. ................................. 514/11
5,037,808  8/1991  Tjoeng et al. .
5,041,380  8/1991  Ruoslahti et al. .

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( x i ) SEQUENCE DESCRIPTION: SEQ ID NO:1:

```
His His Leu Gly Gly Ala Lys Gln Ala Gly Asp Val
 1               5                  10      12
```

( 2 ) INFORMATION FOR SEQ ID NO:2:

( i ) SEQUENCE CHARACTERISTICS:
        ( A ) LENGTH: 10 amino acids
        ( B ) TYPE: amino acid
        ( D ) TOPOLOGY: linear ( x i ) SEQUENCE DESCRIPTION: SEQ ID NO:2:

```
Gly Xaa Gly Arg Gly Asp Ser Pro Cys Ala
 1               5                  10
```

( 2 ) INFORMATION FOR SEQ ID NO:3:

( i ) SEQUENCE CHARACTERISTICS:
        ( A ) LENGTH: 11 amino acids
        ( B ) TYPE: amino acid
        ( D ) TOPOLOGY: linear ( x i ) SEQUENCE DESCRIPTION: SEQ ID NO:3:

```
Gly Xaa Gly His Arg Gly Asp Leu Arg Cys Ala
 1               5                  10  11
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( D ) TOPOLOGY: linear ( x i ) SEQUENCE DESCRIPTION: SEQ ID NO:4:

```
Xaa Arg Gly Asp Xaa
 1               5
```

( 2 ) INFORMATION FOR SEQ ID NO:5:

( i ) SEQUENCE CHARACTERISTICS:
   ( A ) LENGTH: 5 amino acids
   ( B ) TYPE: amino acid
   ( D ) TOPOLOGY: linear ( x i ) SEQUENCE DESCRIPTION: SEQ ID NO:5:

Xaa Lys Gly Asp Xaa
 1               5

PLATELET AGGREGATION INHIBITORS HAVING HIGH SPECIFICITY FOR GPIIBIIIA

This is a continuation of application(s) Ser. No. 08/173,716 filed on Dec. 23, 1993, (abandoned), which application is a continuation of Ser. No. 08/045,566 filed Apr. 9, 1993 (abandoned), which application is a continuation of Ser. No. 07/681,802 filed Apr. 5, 1991 (abandoned).

FIELD OF THE INVENTION

The present invention relates to inhibitors of platelet aggregation. Specifically, the invention is directed to antagonists of the final common pathway of platelet aggregation that act as potent antithrombotics. The invention further relates to therapeutic applications of these inhibitors in diseases for which blocking of platelet aggregation is indicated.

BACKGROUND OF THE INVENTION

Platelets are particles found in whole blood that initiate and provide the structural basis for the hemostatic plug necessary to stop bleeding. Platelets depend on adhesive interactions with extracellular proteins and other cells for proper function. The external platelet plasma membrane surface is covered with a variety of membrane bound glycoproteins, many of which have adhesive functions. Perhaps the most abundant platelet membrane adhesive proteins belong to the integrin superfamily which include the glycoproteins; GP $II_bIII_a$, GP $I_aII_a$, GP $I_cII_a$, GP $I_bIX$, and the fibronectin and vitronectin receptors. Each integrin receptor is an $\alpha\beta$ heterodimer displaying characteristic affinity and specificity toward various extracellular matrix proteins such as; von Willebrand factor (vWF), collagen, entactin, tenascin, fibronectin (Fn), vitronectin (Vn), and laminin, as well as fibrinogen (Fg) and thrombospondin (see Kieffer et al., *Ann. Rev. cell Biol.* 6:329–357(1990) and Ruoslahti, *J. Clin. Invest.* 87:1–5 (1991)). The most abundant integrin found on normal platelet surfaces is GP $II_bIII_a$ comprising about 50,000 molecules per platelet, representing about 2% of the total platelet protein. GP $II_bIII_a$ is a non-covalent, calcium ion dependent heterodimer complex (Jennings, et al., *J. Biol. Chem.* 257:10458 (1982)) and restricted in distribution to platelets and other cells of the megakaryocytic lineage (Kieffer et al., supra ). On activated platelets, GP $II_bIII_a$ binds a number of adhesive proteins with varying affinities; fibrinogen, fibronectin, von Willebrand factor, vitronectin and thrombospondin (Plow et al., *Biochemistry of Platelets*, Phillips and Shuman eds., p. 225–256, Orlando: Academic Press (1986)). It is believed the most important interactions mediating platelet aggregation involve GP $II_bIII_a$ binding with the trinodular fibrinogen and, to a lesser extent, with the filamentous von Willebrand factor (Kieffer et al., supra and Albeda et al., The FASEB Journal, 4:2868–2880 (1990)).

GP $II_bIII_a$ binding to its natural ligands can be inhibited to varying degrees by peptides and proteins containing the amino acid recognition sequences; Arg-Gly-Asp (RGD) (Ruoslahti, supra and EPO 0368486, assigned to Merck & Co.), Lys-Gly-Asp (KGD), and the fibrinogen γ-chain carboxy-terminal dodecapeptide HHLGGAKQAGDV (Seq. ID No. 1) and analogues thereof (Timmons et al., Biochemistry, 28:2919–2922 (1989)).

It is known that, for the RGD recognition sequence, the conformation of the RGD sequence is important for receptor recognition. Pierschbacher et al. (*J. Biol. Chem.* 292:17294–17298 (1987)) found that by cyclizing the peptide Gly-Pen-Gly-Arg-Gly-Asp-Ser-Pro-Cys-Ala (Seq. ID No. 2) through a Pen-Cys disulfide bridge the peptide became 10 times more effective at inhibiting the vitronectin-vitronectin receptor interaction but ineffective at inhibiting the fibronectin-fibronectin receptor interaction when compared to th peptide. Similarly, Kirchofer et al. (*J. Biol. Chem.*, 265 :18525–18530 (1990)) observed that the disulfide bridged cyclic peptide, cyclic- 2,10-GPenGHRGDL-RCA (Seq. ID. No. 5) preferentially inhibits the binding of GP $II_bIII_a$ to fibrinogen but does not inhibit the binding of other RGD-dependent integrins, $\alpha_{v\beta3}$ and $\alpha_{5\beta1}$, to their respective ligands to the same extent. These authors also observed that a smaller "non-disulfide bridged" cyclic peptide, cyclic-1,7-VRGDSPDG, preferentially inhibited $\alpha_{v\beta3}$ (vitronectin receptor) binding to vitronectin.

These results demonstrate that the conformation of the recognition sequence is important to specificity, but do not provide guidance regarding what the proper conformation(s) are and what structural features produce those conformation(s). Many examples of proteins having Arg-Gly-Asp and Lys-Gly-Asp recognition sequences have been reported, each of which, due to primary, secondary and tertiary structural constraints, produces a limited number of conformations about the recognition sequence in a given protein. However, whether these conformations bind to specific integrin receptors or any receptor at all can not be deduced from knowledge of the primary structure and the mere fact that these sequences are constrained. A representative list of some of these recognition sequence containing proteins includes: Maes et al., *Fed. Eur. Biochem. Soc.*, 241(1,2): 41–45 (1988); Moos et al., *Nature*, 334:701–703 (1988); Rauvala et al., *J. Cell Biol.*, 107:2293–2305 (1988); Drickamer et al., *J. Biol. Chem.*, 261:6878–6887 (1986); Bond and Strydom et al., *Biochemistry*, 28:6110–6113 (1989); Ratner et al., *Nature*, 313:277–284 (1985); Davies et al., *Biochem. Soc. Trans.*, 18:1326–1328 (1990); and Neurath et al., *Mol. Immun.*, 27:539–549 (1990).

Similarly, a number of synthetic peptides, including cyclic disulfides, have been disclosed as inhibitors of fibrinogen binding to platelets all of which contain the Arg-Gly-Asp recognition sequence. See U.S. Pat. No. 4,683,291; WO89/05150; EPO 0 319 506 A2; EPO 0 341 915 A2; Plow et al., *Proc. Natl. Acad. Sci.* USA 82: 8057–8061(1985); Ruggeri et al., *Proc. Natl. Acad. Sci.* USA 83, 5708–5712(1986); Haverstick et al., *Blood* 66, 946–952 (1985); (Plow et al., *Blood* 70, 110–115(1987); F. El F. Ali, et al., *Proc. Eleventh Amer. Peptide Symp.* 94–96(1990); and Pierschbacher et al., supra (1987). None of these publications define structural features producing recognition sequence conformations that are specific for various integrin receptors.

Several synthetic cyclic peptides containing linkages other than disulfides, specifically the thioether linkage, have been reported. Gero et al., *Biochem. Biophys. Res. Comm.* 120: 840–845(1984) describe a pseudohexapeptide analog of somatostatin where the group [$CH_2$-S] is substituted for a peptide bond. Similarly, Edwards et al., *Biochem. Biophys. Res. Comm.* 136: 730–736(1986) compare the biological activity of linear and cyclic enkephalin pseudopeptide analogs containing the thiomethylene ether linkage. Other enkephalin related pseudopeptides and macrocycles containing the [$CH_2$-S] substitution for peptides have been described (Spatola et al., *Biopolymers* 25: 229–244(1986) and Spatola et al., *Tetrahedron* 44:821–833(1988). No information is provided in these publications defining conformation(s) these linkages might induce in a cyclic peptide containing those linkages.

The interaction of GP II$_b$III$_a$ with fibrinogen is stimulated by certain factors released or exposed when a blood vessel is injured. Multiple factors, including a variety of physiologic stimuli and soluble mediators, initiate platelet activation via several pathways. These pathways have a common final step which is the activation of the GP II$_b$III$_a$ receptor on the platelet surface and its subsequent binding to fibrinogen followed by aggregation and thrombus formation. By virtue of these interactions GP II$_b$III$_a$ is a component of the platelet aggregation system (Pytela et al., *Science* 231: 1559(1986)). Thus, inhibition of the interaction of GP II$_b$III$_a$ with Arg-Gly-Asp containing ligands such as fibrinogen is a useful means of modulating thrombus formation. An inhibitor which prevents this binding interaction would antagonize platelet aggregation following platelet activation by any stimulus and therefore would have important antithrombotic properties.

Many common human disorders are characteristically associated with a hyperthrombotic state leading to intravascular thrombi and emboli. These are a major cause of medical morbidity, leading to infarction, stroke and phlebitis, and of mortality from stroke and pulmonary and cardiac emboli. Patients with atherosclerosis are predisposed to arterial thromboembolic phenomena for a variety of reasons. Atherosclerotic plaques form niduses for platelet plugs and thrombii that lead to vascular narrowing and occlusion, resulting in myocardial and cerebral ischemic disease. This may happen spontaneously or following procedures such as angioplasty or endarterectomy. Thrombii that break off and are released into the circulation cause infarction of different organs, especially the brain, extremities, heart and kidneys.

In addition to being involved in arterial thrombosis, platelets may also play a role in venous thrombosis. A large percentage of such patients have no antecedent risk factors and develop venous thrombophlebitis and subsequent pulmonary emboli without a known cause. Other patients who form venous thrombi have underlying diseases known to predispose to these syndromes. Some of these patients may have genetic or acquired defidencies of factors that normally prevent hypercoagulability, such as antithrombin-3. Others have mechanical obstructions to venous flow, such as tumor masses, that lead to low flow states and thrombosis. Patients with malignancy have a high incidence of thrombotic phenomena for unclear reasons. Antithrombotic therapy in this situation with currently available agents is dangerous and often ineffective.

Patients whose blood flows over artifidal surfaces, such as prosthetic synthetic cardiac valves or through extracorporeal perfusion devices, are also at risk for the development of platelet plugs, thrombii and emboli. It is standard practice that patients with artificial cardiac valves be chronically anti-coagulated. However, in all instances, platelet activation and emboli formation may still occur despite adequate anticoagulation treatment.

Thus, a large category of patients, including those with atherosclerosis, coronary artery disease, artificial heart valves, cancer, and a history of stroke, phlebitis, or pulmonary emboli, are candidates for limited or chronic antithrombotic therapy. The number of available therapeutic agents is limited and these, for the most part, act by inhibiting or reducing levels of circulating clotting factors. These agents are frequently not effective against the patient's underlying hematologic problem, which often concerns an increased propensity for platelet aggregation and adhesion. They also cause the patient to be susceptible to abnormal bleeding. Available antiplatelet agents, such as aspirin, inhibit only part of the platelet activation process and are therefore often inadequate for therapy and also cause the patient to be susceptible to abnormal bleeding.

An agent which effectively inhibits the final common pathway of platelet activation, namely fibrinogen binding to the GP II$_b$III$_a$ receptor, should accordingly be useful in a large group of disorders characterized by a hyperthrombotic state as described above. The present invention contemplates such agents which are new compositions, namely cyclic polypeptides consisting in part of natural amino acids and in part of unnatural amino acids. These new compositions interfere with the interaction of Arg-Gly-Asp containing peptides and proteins, particularly fibrinogen, with the GP II$_b$III$_a$ complex thereby preventing platelet aggregation. Platelet aggregation has been identified as an early step in the formation of platelet plugs, emboli and thrombii in the circulatory system which in turn have been shown to play an active role in cardiovascular complications and disease. Inhibition of fibrinogen binding to the GP II$_b$III$_a$ complex has been shown to be an effective antithrombotic treatment in animals (H. K. Gold, et al., *Circulation* 77: 670–677(1988); T. Yasuda, et al., *J. Clin. Invest.* 81: 1284–1291(1988); B. S. Coller, et al., *Blood* 68: 783–786(1986)).

None of the foregoing references disclose a compound capable of potent platelet aggregation inhibition activity and low inhibitory activity for the adhesive interaction of vitronectin-vitronectin receptor, fibronectin-fibronectin receptor, and GP II$_b$III$_a$ receptor with ligands other than fibrinogen. Furthermore, none of these references disclose potent platelet aggregation inhibitors that do not produce untoward side effects such as increased cutaneous bleeding time or decreased peripheral blood flow.

Accordingly, it is an object of this invention to produce compounds having potent platelet aggregation inhibition activity. It is another object of the invention to produce such compounds that are stable to degradation. It is a further object to produce potent platelet aggregation inhibitors that are specific and do not strongly inhibit RGD sensitive other integrin interactions including the Vn-VnR, Fn-FnR, and GP II$_b$III$_a$-vWF interactions. It is still a further object to produce potent platelet aggregation inhibitors that do not significantly increase cutaneous bleeding time or diminish other hemodynamic factors. These and other objects of this invention will be apparent from consideration of the invention as a whole.

SUMMARY OF THE INVENTION

The objects of this invention are accomplished by providing a peptide comprising:

(a) a cyclic moiety containing a sequence selected from

Xaa$_1$-Arg-Gly-Asp-Xaa$_2$, and (Seq. ID. No. 5)

Xaa$_1$-Lys-Gly-Asp-Xaa$_2$ (Seq. ID. No. 5)

where Xaa$_1$ represents from 1 to 20 α-amino acids or α-amino acid analogues, and Xaa$_2$ represents an α-amino acid or α-amino acid analogue bonded to Xaa$_1$ through a linkage selected from the group amide, thioether, disulfide, ether, sulfoxide, and sulfone, and (b) a positively charged nitrogen containing exocyclic moiety bonded to Xaa$_2$ through a carbonyl group of Xaa$_2$.

Preferably the peptide contains a positively charged exocyclic moiety is represented by the formula:

—NH-(link)-q where (link) represents a linking group selected from $C_3$–$C_{10}$-alkyl either branched, linear, or cyclic, $C_3$–$C_{10}$-alkenyl, $C_6$–$C_{14}$-aryl substituted with 2 or more $C_1$–$C_8$-alkyl groups, $C_5$–$C_{14}$-heterocycle, saturated or unsaturated, containing from 1–4 heteroatoms selected from N, O, and S, $C_1$–$C_6$-alkyl substituted $C_5$–$C_{14}$, saturated or unsaturated heterocycle, containing from 1–4 heteroatoms selected from N, O, and S, and optionally, (link) may be substituted with substituents selected from COR, CONR'R", halo (F,Cl,Br,I), nitro, $C_1$–$C_6$-alkyl, phenyl, benzyl, and $C_3$–$C_6$-cycloalkyl, where R is selected from one or more of the groups hydroxy, $C_1$–$C_8$-alkoxy, $C_3$–$C_{12}$-alkenoxy, $C_6$–$C_{12}$-aryloxy, di-$C_1$–$C_8$-alkylamino-$C_1$–$C_8$-alkoxy, acylamino-$C_1$–$C_8$-alkoxy selected from the group acetylaminoethoxy, nicotinoylaminoethoxy, succinamidoethoxy, and pivaloyloxyethoxy, $C_6$–$C_{12}$-aryl-$C_1$–$C_8$-alkoxy where the aryl group is unsubstituted or substituted with one or more of the groups nitro, halo (F, Cl, Br, I), $C_1$–$C_4$-alkoxy, and amino, hydroxy-$C_2$–$C_8$-alkoxy, dihydroxy-$C_3$–$C_8$-alkoxy, and where R' and R" are independently selected from hydrogen, $C_1$–$C_{10}$-alkyl either branched, linear, or cyclic, $C_3$–$C_{10}$-alkenyl, $C_6$–$C_{14}$-aryl, $C_1$–$C_6$-alkyl-$C_6$–$C_{10}$-aryl, saturated or unsaturated heterocycle having from 5–14 atoms in the cycles and from 1–4 heteroatoms selected from N, O, and S, optionally, R' and R" taken together may for trimethylene, tetramethylene, pentamethylene, and 3-oxopentamethylene, q represents a group selected from amino, amidino, and guanido, where any hydrogen bonded to any nitrogen or carbon of the amino, amidino, or guanido group is optionally substituted with a lower $C_1$–$C_6$-alkyl group.

Typically, the positively charged exocyclic moiety is a positively charged amino acid residue selected from α-amino acids or α-amino acid analogues. These include either D or L, His, Lys, Arg or Orn, where the α-carboxyl group is derivitized with an amino or lower alkyl substituted amino group.

Also typically, $Xaa_2$ will be an amino acid residue selected from α-aminoadipic, Cys, homo-Cys, Pen, Pas, Asp, Glu, Orn, Lys, Ser, Thr and Tyr. Most preferably, $Xaa_2$ will be selected from Cys and Pen. $Xaa_1$ preferably is a single amino acid selected from Gly, D-Ala, D-Val, D-Leu, D-Ile, D-Phe, D-Tyr and D-Pro and the linkage bonding $Xaa_1$ with $Xaa_2$ will be a thioether or sulfoxide.

The preferred compound of this invention is represented by Formula I:

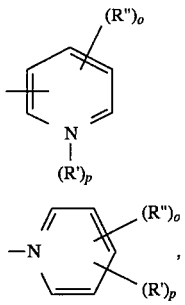

Formula I where $R_1$ is selected from $NHR_{15}Q$, and $NR_{15}R_{16}Q$, where $R_{15}$ and $R_{16}$ are independently selected from $C_3$–$C_{10}$-alkyl either linear, branched or cyclic, $C_3$–$C_{10}$-alkenyl, $C_6$–$C_{14}$-aryl, $C_1$–$C_6$-alkyl-$C_6$–$C_{10}$-aryl, saturated or unsaturated heterocycle or $C_1$–$C_6$-alkyl substituted heterocycle containing from 5 to 14 atoms in the cycle and from 1 to 4 heteroatoms selected from N, O and S, $NR_{15}R_{16}$ taken together may form a heterocycle or $C_2$–$C_6$-alkyl substituted heterocycle where $R_{15}$ and $R_{16}$ taken together are trimethylene, tetramethylene, pentamethylene or 3oxopentamethylene, and where each $R_{15}$ or $R_{16}$ may optionally be substituted with one or more substituents selected from $COR_9$, CONR'R", halo (F,Cl, Br,I), nitro, $C_1$–$C_6$-alkyl, phenyl, benzyl and $C_3$–$C_6$-cycloalkyl, and Q is a group bonded to $R_{15}$, $R_{16}$ or substituents bonded thereto, Q being selected from:

—NR'R"

—NR'R"R'"

—NR'—C=NR'
         |
         NR'R"

—NR'—CR"=NR'

—NR'—CR'=NR"

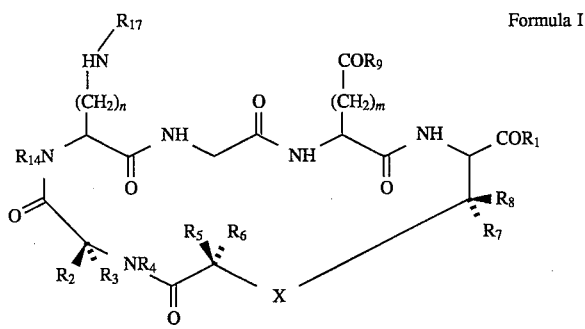

where R' and R" are independently selected from hydrogen, $C_1$–$C_{10}$-alkyl either branched, linear, or cyclic, $C_3$–$C_{10}$-alkenyl, $C_6$–$C_{14}$-aryl, $C_1$–$C_6$-alkyl-$C_6$–$C_{10}$-aryl, saturated or unsaturated heterocycle having from 5–14 atoms in the cycles and from 1–4 heteroatoms selected from N, O and S, and where R' and R" taken together are trimethylene, tetramethylene, pentamethylene, and 3-oxopentamethylene, and where R'" is $C_1$–$C_{10}$-alkyl, phenyl and benzyl, and o and p together are an integer selected form 0, 1, 2, 3, and 4.

The term "functional group" when applied to amino acids and amino acid analogues refers to α-carboxyl, α-amino, and side-chain groups selected from the substituents of $R_1$, $R_2$ and $R_3$ as defined above. Typically, these substituents will be groups such as amino, amidino, guanidino, mercapto, hydroxy, carboxy, halo and aldehyde. These functional groups are capable of forming a bond with a compatible functional group of a second molecule.

$R_2$, $R_3$, $R_5$, $R_6$, $R_7$, $R_8$ are the same or different and are selected from hydrogen, $C_6$–$C_{12}$-aryl where the aryl group is unsubstituted or substituted, $C_1$–$C_{12}$-alkyl, either substituted or unsubstituted, branched or straight chain, aromatic heterocycle where the heterocycle contains 5–10 ring atoms and one or two O, N or S heteroatoms;

$R_2$ and $R_3$, $R_5$ and $R_6$, or $R_7$ and $R_8$ may optionally and independently be joined together to form a carbocyclic or heterocyclic ring of from four to seven atoms where the heteroatoms are selected from O, S or $NR_{12}$;

where $R_{12}$ is selected from hydrogen, $C_1$–$C_8$-alkyl, $C_3$–$C_8$-alkenyl, $C_6$–$C_{12}$-aryl, $C_6$–$C_{12}$-aryl-$C_1$–$C_8$-alkyl, $C_1$–$C_8$-alkanoyl a $C_6$–$C_{12}$-aroyl, and;

$R_4$ is selected from hydrogen, $C_1$–$C_8$-alkyl, $C_3$–$C_{10}$-cycloalkyl, $C_6$–$C_{12}$-aryl, and $C_6$–$C_{12}$-aryl-$C_1$–$C_8$-alkyl;

$R_2$ or $R_3$ may be optionally joined with $R_4$ to form a piperidine, pyrrolidine or thiazolidine ring;

$R_9$ is selected from hydroxy, $C_1$–$C_8$-alkoxy, $C_3$–$C_{12}$-alkenoxy, $C_6$–$C_{12}$-aryloxy, di-$C_1$–$C_8$-alkylamino-$C_1$–$C_8$-alkoxy, acylamino-$C_1$–$C_8$-alkoxy selected from the group acetylaminoethoxy, nicotinoylaminoethoxy, and succinamidoethoxy, pivaloyloxyethoxy, $C_6$–$C_{12}$ aryl-$C_1$–$C_8$-alkoxy where the aryl group is unsubstituted or substituted with one or more of the groups nitro, halo (F, Cl, Br, I), $C_1$–$C_4$-alkoxy, and amino, hydroxy-$C_2$–$C_8$-alkoxy, dihydroxy-$C_3$–$C_8$-alkoxy, and $NR_{10}R_{11}$, where $R_{10}$ and $R_{11}$ are the same or different and are hydrogen, $C_1$–$C_8$-alkyl, $C_3$–$C_8$-alkenyl, $C_6$–$C_{12}$-aryl, where the aryl group is unsubstituted or substituted with one or more of the groups nitro, halo (F, Cl, Br, I), $C_1$–$C_4$-alkoxy, and amino, $C_6$–$C_{12}$-aryl-$C_1$–$C_8$-alkyl, where the aryl group is unsubstituted or substituted by one or more of the groups nitro, halo (F, Cl, Br, I), $C_1$–$C_4$-alkoxy, and amino;

$R_{14}$ is selected from hydrogen, $C_1$–$C_8$-alkyl, $C_3$–$C_8$-alkenyl, $C_6$–$C_{12}$-aryl, and $C_6$–$C_{12}$-aryl-$C_1$–$C_8$-alkyl;

$R_{17}$ is selected from hydrogen, and

X is selected from O or S, S bearing one or two O atoms, $NR_{13}$ where $R_{13}$ is hydrogen, $C_1$–$C_8$-alkyl, $C_3$–$C_8$-alkenyl, $C_6$–$C_{14}$-aryl, $C_6$–$C_{14}$-aryl-$C_1$–$C_8$-alkyl, $C_1$–$C_8$-alkanoyl, $C_6$–$C_{14}$-aroyl, $C_6$–$C_{14}$-aryl-$C_1$–$C_8$-alkanoyl and $(CH_2)_k$, where k is an integer from 0 to 5, n is an integer from 1 to 6, and m is an integer from 0 to 4.

As used herein and unless specified otherwise, alkyl, alkenyl and alkynyl denote straight and branched hydrocarbon chains having single, double and triple bonds, respectively; $C_6$–$C_{12}$ aryl groups denote unsubstituted aromatic ring or fused rings such as, for example, phenyl or naphthyl; hetero denotes the heteroatoms O, N or S; aromatic heterocyclic groups have 5–10 ring atoms and contain up to four heteroatoms; halogen or halo denote F, Cl Br or I atoms; and alkoxy denotes an alkyl group attached to O.

Examples of $C_1$–$C_8$ alkyl or $C_2$–$C_8$ alkenyl groups include methyl, ethyl, propyl, isopropyl, butyl, t-butyl, pentyl, isopentyl, hexyl, vinyl, allyl, butenyl and the like; examples of $C_3$–$C_{10}$-cycloalkyl groups include cyclopropyl, cyclopentyl, cyclohexyl, and the like; aromatic heterocyclic groups include but are not limited to pyridyl, thienyl, furyl, indolyl, benzthienyl, imidazolyl, thiazolyl, quinolinyl and isoquinolinyl.

The present invention also includes a method for reducing platelet aggregation in a mammal. This method involves administering a therapeutically effective amount of the compounds of the present invention alone or in combination with a pharmacologically acceptable carrier. This general method may also be applied to treat a mammal having an increased propensity for thrombus formation.

Additionally, the present invention is directed to compositions of matter for reducing platelet aggregation in a mammal; treating a mammal having an increased propensity for thrombus formation; or inhibiting binding of a ligand to GP $II_bIII_a$ in a mammal; wherein each of these compositions contains as an active ingredient one or more of the cyclic peptides defined in Formula I.

DETAILED DESCRIPTION OF THE INVENTION

Definitions

Unless otherwise specified, the following definitions apply to the terms used throughout this specification.

By the term "α-amino acid" as used herein is meant naturally occurring α-amino acids encoded by mRNA and incorporated into polypeptides as they are synthesized on the ribosome. Except for glycine, these α-amino acids are chiral and of the L-stereoisomeric form.

The term "unnatural" α-amino acids is used to denote the D-isomeric form of the naturally occurring L-α-amino acids.

By the term "α-amino acid analogues" as used herein is meant those α-amino acids, other than the naturally occurring α-amino acids, represented by the formula:

Where $R_1$ is selected from hydrogen and $C_1$–$C_6$-alkyl. $R_2$ and $R_3$ are the same or different and are selected from: $C_1$–$C_{12}$-alkyl either linear branched or cyclic; $C_2$–$C_{12}$-alkenyl branched linear or cyclic; $C_2$–$C_{12}$-alkynyl; $C_6$–$C_{14}$-aryl, $C_1$–$C_8$-alkyl-$C_6$–$C_{14}$-aryl, $C_1$–$C_{13}$-heterocycle either saturated or unsaturated, the cycle(s) containing from 1–4 heteroatoms selected from N, O, and S; $C_1$–$C_6$-alkyl-$C_1$–$C_{13}$-heterocycle either saturated or unsaturated, the cycle(s) containing from 1–4 heteroatoms selected from N, O, and S; $R_1$ and $R_2$ or $R_2$ and $R_3$ taken together may form a carbocyclic or heterocyclic ring containing from 5 to 14 atoms of which from 1–4 heteroatoms are selected from N, O, or S. $R_1$, $R_2$ or $R_3$ may optionally be substituted with one or more substituents selected from:

halo(F, Cl, Br, I)

—OR'

—SR'

—COOR'

—CONR'R"

—NR'R"

—NR'R"R'"

—NR'—C=NR'
      |
      NR'R"

—NR'—CR"=NR'

—NR'—CR'=NR"

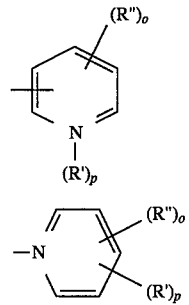

where R' and R" are independently selected from: hydrogen; $C_1$–$C_{10}$-alkyl either branched, linear, or cyclic; $C_3$–$C_{10}$-alkenyl; $C_6$–$C_{14}$-aryl; $C_1$–$C_6$-alkyl-$C_6$–$C_{10}$-aryl; saturated or unsaturated heterocycle having from 5–14 ring atoms and from 1–4 heteroatoms selected from N, O, and S; and where R' and R" taken together may form a bridging functionality to produce a heterocycle, e.g., trimethylene, tetramethylene, pentamethylene, and 3-oxopentamethylene. R'" is $C_1$–$C_{10}$-alkyl, phenyl or benzyl and o and p together are an integer selected form 0, 1, 2, 3, and 4.

The following one-letter and three-letter abbreviations for α-amino acids and α-amino acid analogues are used herein as follows:

| One-Letter Code | Three-Letter Code | Common Name |
|---|---|---|
| α-amino acids | | |
| A | Ala | alanine |
| R | Arg | arginine |
| N | Asn | asparagine |
| D | Asp | aspartic acid |
| C | Cys | cysteine |
| Q | Gln | glutamine |
| E | Glu | glutamic acid |
| G | Gly | glycine |
| H | His | histidine |
| I | Ile | isoleucine |
| L | Leu | leucine |
| K | Lys | lysine |
| M | Met | methionine |
| F | Phe | phenylalanine |
| P | Pro | proline |
| S | Ser | serine |
| T | Thr | theonine |
| W | Trp | tryptophan |
| Y | Tyr | tyrosine |
| V | Val | valine |
| α-amino acid analogues | | |
| | Aad | α-aminoadipic acid |
| | Aib | α-aminoisobutyric acid |
| | Cha | Cyclohexylalanine |
| | Naa | naphthylalanine |
| | Nle | norleucine |
| O | Orn | ornithine |
| | Pas | 6,6-cyclopentamethylene-2-aminosuberic acid |
| | Pen | penicillamine |
| | Pmt | ρ-methyltyrosine |
| | SuA | succinylalanine |

When capitalized, the one-letter code as used herein refers to the L or natural form of the amino acid. The corresponding lower case letter refers to the unnatural or D form of the α-amino acid or analogue.

As used herein, the term "cyclic moiety" refers to a peptide having an intramolecular bond between two adjacent amino acids within a peptide, that would not be adjacent in the absence of that bond. The intramolecular bond includes, but is not limited to; backbone to backbone, side-chain to backbone and side-chain to side-chain cyclizations.

The cyclic moiety includes the peptide bonds linking one amino acid or amino acid analogue residue with another as well as the side-chains of those amino acids or amino acid analogues. The cyclic moiety may also contain other intermolecular bonds including amide, thioether, disulfide, ether, sulfoxide, sulfone and carbon-carbon bonds. The cyclic moiety may also contain groups other than amino acid and amino acid analogue residues such as acetyl or phenylacetyl groups used to form the cycle.

The term "exocyclic moiety" as used herein refers to a group having a bond connecting the group to a cycle, where breaking the bond would not destroy the cycle. By way of illustration, the exocyclic moiety may form a peptide bond by linking with an α-amino or α-carboxy of the cyclic moiety. Alternatively, the exocyclic moiety may be linked through an amide bond with the γ or δ carboxyl, or δ or ε amino side-chain groups of the cyclic moiety amino acid residues. Other side-chain linkages between the cyclic and exocyclic moieties may include ester and thioester, ether and thioether, aldimine, disulfide, sulfoxide, sulfone, and the like. Preferably, the exocyclic moiety will be bonded through an α, β, γ, δ, ε, or higher carboxyl group of an α-amino acid or α-amino acid analogue of the cyclic moiety. Most preferably, the exocyclic moiety will be bonded to the cyclic moiety through an α-carboxyl group.

As used herein, the term "peptide bond" refers to an amide bond between the α-carboxyl group of one α-amino acid or α-amino add analogue and the α-amino group of another α-amino acid or α-amino acid analogue.

As used herein, the term "amide bond" is used to indicate any carboxy-amino bond other than α-carboxy-α-amino bond between α-amino acids and analogues.

Preferred Embodiments

The instant invention is a result of the unexpected discovery, that by bonding a positively charged exocyclic moiety to a cyclic peptide containing the tripeptide recognition sequences RGD or KGD, a potent platelet aggregation inhibitor is produced that is highly specific for the platelet GP $II_bIII_a$ receptor but which does not exhibit many of the in vivo side effects observed with other potent GP $II_bIII_a$ inhibitors.

The exocyclic moiety is typically positively charged at physiological pH (ca 7.4) and contains a nitrogen atom preferably as a substituted (alkyl) or unsubstituted amino, amidino or guanido functional group. Preferably, the exocyclic moiety will be a positively charged amino acid residue such as Lys, Arg or Orn, where the α-carboxyl is in the amide or uncharged form, and the α-amino group is linked to a carboxyl group of the cyclic moiety by a peptide or amide bond. Alternatively, the positive charge may be provided by linking a non-peptidyl group such as an alkylene diamine, e.g., ethylenediamine-octamethylene diamine, with a free α-carboxyl group of the cyclic moiety.

The positively charged exocyclic moiety is bonded to the amino acid residue immediately following the RGD or KGD recognition sequence. Thus, the amino acid residue following the recognition sequence acts as a "branch point" both connecting the recognition sequence to the positively charged exocyclic moiety and participating in the formation of the cycle.

In one embodiment, the amino acid residue following the recognition sequence will (a) form a peptide or amide bond through its α-carboxyl group with the positively charged exocyclic group and (b) form a cycle through a functional group on the side-chain of that amino add with either the α-amino group of the Lys or Arg of the recognition sequence or to a functional group of an amino acid or analogue on the amino side of the recognition sequence. In this embodiment, the cyclic moiety will contain, in addition to peptide bonds, a side-chain bridging bond typically selected from amide, ether, thioether, sulfoxide, sulfone and disulfide.

In an alternative embodiment, the amino acid residue following the recognition sequence will (a) bond the exocyclic moiety through a side-chain functional group of that amino acid and (b) form the cycle through the α-carboxyl group of that amino acid residue. In this embodiment the cycle may contain all peptide bonds e.g., backbone-backbone bridge) or may form a cycle through side-chain-side-chain or side-chain-backbone bridges between other amino acid residues.

To be suitable for use as an antithrombotic agent, a cyclic peptide should be a potent inhibitor of platelet aggregation, that is, it must possess in $IC_{50}$ in a human platelet agregation inhibition assay of no more than at least about 3 μM. Preferably, the cyclic peptide will inhibit platelet aggregation with an $IC_{50}<1$ μM and most preferably the $IC_{50}$ will range from about 100 to 500 nM.

In addition to being potent, the cyclic peptide should be specific, that is, not strongly inhibit the interaction of other integrin receptors for their natural ligands, or the interaction between GP $II_bIII_a$ and ligands other than fibrinogen. Thus, the preferred cyclic peptide should not strongly inhibit the interaction between GP $II_bIII_a$ and von Willebrand factor (vWF). Thus, in a vWF-GP II$_b$III$_a$ ELISA, as described herein, the preferred cyclic peptide should give an IC$_{50}$>1 nM, more preferably IC$_{50}$>10 nM, and most preferably the IC$_{50}$ should range from at least about 15 nM to about 75 nM. Also preferably, the cyclic peptide should not strongly inhibit the interaction between Vitronectin (Vn) and the Vitronectin receptor $\alpha_v\beta_3$ (VnR). Thus, in a Vn-VnR ELISA assay, as described herein, the preferred cyclic peptide should possess an IC$_{50}$>10 nM, more preferably IC$_{50}$>50 nM and most preferably IC$_{50}$≧20 μM. Similarly, a preferred cyclic peptide should not strongly inhibit the fibronectin-fibronectin receptor interaction.

Finally, in addition to being small, potent and specific, the preferred cyclic peptide platelet aggregation inhibitor should not produce substantial untoward in vivo side effects such as an increased cutaneous bleeding time, reduction in platelet count, or decreased peripheral blood flow in a mammal treated with the inhibitor. Thus, for example, the time it takes for bleeding to stop, on an incision made in a mammal treated with a platelet aggregation inhibitor, dosed to inhibit about 90–100% of platelet aggregation, should not be more than about twice that of the mammal prior to treatment. Similarly, peripheral blood flow and other hemodynamic factors should not be adversely affected by treatment with doses sufficient to achieve 90–100% inhibition of platelet aggregation.

The compounds of this invention, containing the recognition sequences RGD or KGD in a cycle and bearing an exocyclic positively charged group bonded to the amino acid immediately following the Asp residue, have been found to be potent, specific and not to exhibit any untoward in vivo side effects at appropriate doses. The following discussion will be more readily understood by referring to Example 12 where the structures of the various compounds and the assay results are tabulated. The numerical designations used to identify the compounds refer to the example number/compound number as provided in the Examples section. The small cyclic peptides (7/46) and (7/47) shown below containing the RGD and KGD recognition sequences respectively, are potent inhibitors of platelet aggregation. Peptide (7/46) and peptide (7/47) have IC$_{50}$'s for platelet aggregation inhibition of 150 nM and 480 nM, respectively.

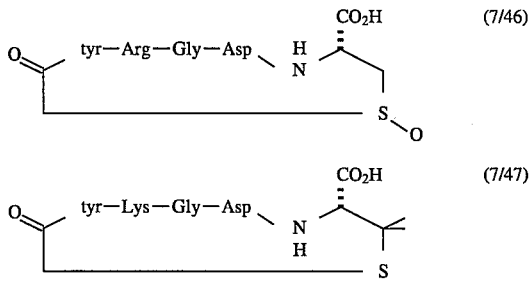

Compound (7/46) however is not a specific inhibitor of the fibrinogen-GP II$_b$III$_a$ interaction; rather, it potently inhibits both the GP II$_b$III$_a$-vWF interaction (IC$_{50}$=0.18 nM) and the Vn-VnR interaction (IC$_{50}$=5 nM). Compound (7/47), while not inhibiting the Vn-VnR interaction (IC$_{50}$>20 μM), is a fairly potent inhibitor of the GP II$_b$III$_a$-vWF interaction (IC$_{50}$=1.0 nM). More importantly, however, both of these compounds exhibit an undesired side effect, namely, prolongation of bleeding time in vivo in both the rabbit and dog model. For example, in rabbit, a dose of compound (7/46 or 7/47) sufficient to achieve about 97% inhibition of platelet aggregation, increased cutaneous bleeding time 8.0 and 8.6 times, respectively when compared to the undosed animal.

By adding an exocyclic positively charged moiety to the cyclic structures of either compound (7/46) or (7/47), more potent and more specific platelet aggregation inhibitors that do not substantially increase cutaneous bleeding time or decrease peripheral blood flow are obtained. Compounds (7/1), (7/3), (7/17), and (7/16) below, exemplify this result.

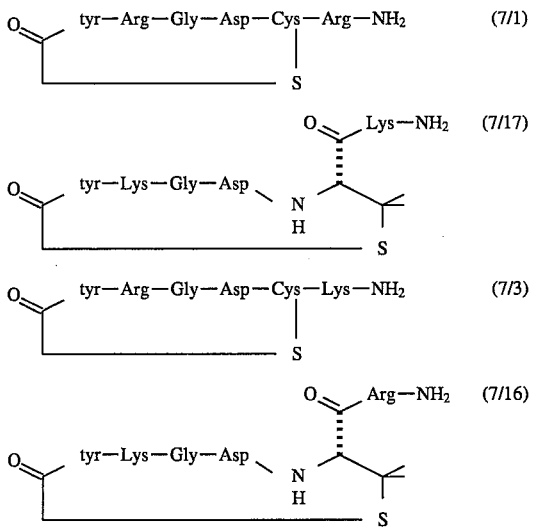

Bonding the arginylamide to the free carboxy residue of a compound of the (7/46) type produces compound (7/1) which exhibits high potency (IC$_{50}$=80 nM in the platelet aggregation assay), high specificity (IC$_{50}$=13.8 in the GPI-I$_b$III$_a$-vWF ELISA), and no substantial increase in cutaneous bleeding time (1.17 times; dosed to 100% inhibition of platelet aggregation) or decrease in peripheral blood flow. Similarly, adding the positively charged lysylamide residue to a compound of the (7/46) type produces compound (7/3) which is highly potent (IC$_{50}$=320 nM in the platelet aggregation assay), highly specific (IC$_{50}$=15.9 nM in the GPI-I$_b$III$_a$-vWF ELISA), and which does not substantially increase cutaneous bleeding time (1.95 times; dosed to 95% inhibition of platelet aggregation).

Compounds of the (7/47) type, that is containing the Lys-Gly-Asp sequence in the cycle, also exhibit the dramatically improved pharmacological properties upon adding an exocyclic positively charged group. Both compounds (7/17) and (7/16) containing an exocyclic lysylamide and arginylamide residue display high potency in the platelet aggregation assay (i.e. IC$_{50}$ of 90 nM and 500 nM respectively), the highest specificity yet observed in the Vn-VnR, Fn-FnR, and GP II$_b$III$_a$ELISA's, without substantial increased cutaneous bleeding time or decreased peripheral blood flow.

Various controls were tested in the same assays to ascertain whether the observed effect was due to the positively charged exocyclic moiety. Compound (7/27), which contains an uncharged exocyclic hydrogen-bond donor/receptor (Gln-NH$_2$), did not increase cutaneous blood time; however, it did not significantly improve potency. It is contemplated, however, compound (7/27) may be modified, for example, by forming the sulfoxide or by substituting Pen for Cys to increase platelet aggregation inhibition potency. Compound (7/28), which contains a negatively charged exocyclic moiety (5-aminovaleric acid), exhibited a pronounced decrease in platelet aggregation inhibition (IC$_{50}$=52.2 μM).

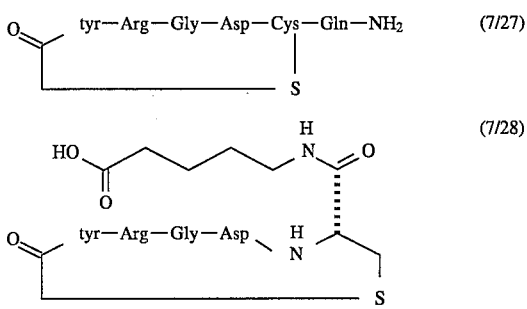

Other positively charged non-peptidyl exocyclic groups also conferred high potency and specificity on cyclic peptides containing the tripeptide recognition sequences while not increasing cutaneous bleeding time. Exocyclic alkylene diamine groups as short as ethylenediamine produced the same effects. Similarly, inserting the amino acid residue Tyr between the positively charged exocyclic Arg and the bridging amino acid residue following the recognition sequence did not substantially decrease potency.

Methods for Making Platelet Aggregation Inhibitors

Polypeptides of this invention can be made by chemical synthesis or by employing recombinant technology. These methods are known to those of ordinary skill in the protein or peptide synthesis art. Chemical synthesis, especially solid phase synthesis, is preferred for short (e.g. less than 50 residues) polypeptides or those containing unnatural or unusual amino adds such as; D-Tyr, Ornithine, aminoadipic add, and the like. Recombinant procedures are preferred for longer polypeptides or for mutant or variant peptides containing the KGD or RGD sequence.

When recombinant procedures are selected, a synthetic gene may be constructed de novo or a natural gene may be mutanigized by, for example, cassette mutagenesis. Set forth below are exemplary general recombinant and chemical procedures.

General Recombinant Procedures

From a purified peptide or protein and its amino acid sequence, a KGD or RGD-containing peptide or protein may be produced using standard recombinant DNA techniques. These techniques contemplate, in simplified form, taking the gene, either natural or synthetic, for the peptide or protein; inserting it into an appropriate vector; inserting the vector into an appropriate host cell; culturing the host cell to cause expression of the gene; and purifying the peptide or protein produced thereby.

Somewhat more particularly, the DNA sequence encoding a KGD or RGD-containing peptide or protein is cloned and manipulated so that it may be expressed in a convenient host. DNA encoding parent polypeptides can be obtained from a genomic library, from cDNA derived from mRNA from cells expressing the peptide or protein, or by synthetically constructing the DNA sequence (Sambrook, J., Fritsch, E. F., and Maniatis, T., (1989), *Molecular Cloning* (2d ed.), Cold Spring Harbor Laboratory Press, N.Y.).

The parent DNA is then ligated into an appropriate plasmid or vector which is used to transform a host cell. In general, plasmid vectors containing replication and control sequences which are derived from species compatible with the host cell are used in connection with those hosts. The vector ordinarily carries a replication site, as well as sequences which encode peptides or proteins that are capable of providing phenotypic selection in transformed cells.

For example, *E. coli* may be transformed using pBR322, a plasmid derived from an *E. coli* species (Mandel, M. et al. (1970) *J. Mol. Biol.* 53, 154). Plasmid pBR322 contains genes for ampicillin and tetracycline resistance, and thus provides easy means for selection. Other vectors include different features such as different promoters, which are often important in expression. For example, plasmids pKK223-3, pDR720, and pPL-lambda represent expression vectors with the tac, trp, or $P_L$ promoters that are currently available (Pharmacia Biotechnology).

A preferred vector is pB0475. This vector contains origins of replication for phage and *E. coli* which allow it to be shuttled between such hosts, thereby facilitating both mutagenesis and expression (Cunningham, B., et al. (1989), *Science* 243, 1330–1336; Wells, J. and Cunningham, B., co-pending application U.S. Ser. No. 07/428,066 filed 26 Oct. 1989. Other preferred vectors are pR1T5 and pR1T2T (Pharmacia Biotechnology). These vectors contain appropriate promoters followed by the Z domain of peptide or protein A, allowing genes inserted into the vectors to be expressed as fusion peptides or proteins. Further discussion of these vectors may be found below.

Other preferred vectors can be constructed using standard techniques by combining the relevant traits of the vectors described above. Relevant traits include the promoter, the ribosome binding site, the target gene or gene fusion (the Z domain of peptide or protein A and the target gene and its linker), the antibiotic resistance markers, and the appropriate origins of replication.

The host cell may be prokaryotic or eukaryotic. Prokaryotes are preferred for cloning and expressing DNA sequences to produce parent polypeptides, segment substituted polypeptides, residue-substituted polypeptides and polypeptide variants. For example, *E. coli* K12 strain 294 (ATCC No. 31446) may be used as *E. coli* B, *E. coli* X1776 (ATCC No. 31537), and *E. coli* c600 and c600hfl, *E. coli* W3110 (F-, gamma-, prototrophic/ATCC No. 27325), bacilli such as *Bacillus subtilis*, and other enterobacteriaceae such as *Salmonella_typhimurium* or *Serratia marcesans*, and various pseudomonas species. The preferred prokaryote is *E. coli* W3110 (ATCC 27325). When expressed by prokaryotes the polypeptides typically contain an N-terminal methionine or a formyl methionine and are not glycosylated. In the case of fusion peptides or proteins, the N-terminal methionine or formyl methionine resides on the amino terminus of the fusion peptide or protein or the signal sequence of the fusion peptide or protein. These examples are, of course, intended to be illustrative rather than limiting.

In addition to prokaryotes, eukaryotic organisms, such as yeast cultures, or cells derived from multicellular organisms may be used. In principle, any such cell culture is workable. However, interest has been greatest in vertebrate cells, and propagation of vertebrate cells in culture (tissue culture) has become a reproducible procedure (*Tissue Culture*, Academic Press, Kruse and Patterson, editors (1973)). Examples of such useful host cell lines are VERO and HeLa cells, Chinese Hamster Ovary (CHO) cell lines, W138, 293 (ATCC #CRL 1573), BHK, COS-7 and MDCK cell lines.

Gene Fusions

A variation on the above procedures contemplates the use of gene fusions, wherein the gene encoding the desired peptide or protein is associated, in the vector, with a gene encoding another peptide or protein or a fragment of another peptide or protein. This results in the desired peptide or protein—here, a KGD or RGD-containing peptide or protein—being produced by the host cell as a fusion with another peptide or protein. The "other" peptide or protein is often a protein or peptide which can be secreted by the cell, making it possible to isolate and purify the desired peptide or protein from the culture medium and eliminating the necessity of destroying the host cells which arises when the desired peptide or protein remains inside the cell. Alternatively, the fusion peptide or protein can be expressed intracellularly. It is useful to use fusion peptides or proteins that are highly expressed.

The use of gene fusions, though not essential, can facilitate the expression of heterologous peptides or proteins in *E. coli* as well as the subsequent purification of those gene products (Harris, T. J. R. (1983) in *Genetic Engineering*, Williamson, R., Ed., Academic, London, Vol. 4, p. 127; Uhlen, M., Moks, To. (1989) *Methods Enzymol.* (in press)). Protein A fusions are often used because the binding of protein A, or more specifically the Z domain of protein A, to IgG provides an "affinity handle" for the purification of the fused peptide or protein. It has also been shown that many heterologous peptides or proteins are degraded when expressed directly in *E. coli*, but are stable when expressed as fusions (Marston, F. A. O., (1986) *Biochem J.* 240, 1).

A KGD or RGD-containing peptide or protein expressed as a fusion peptide or protein may be properly folded or may require folding or crosslinking to obtain the native structure. The properly folded fusion peptide or protein may be active and useful as a GP $II_b III_a$ antagonist and inhibitor of platelet aggregation. More preferred would be the correctly folded "native" peptide or protein that is obtained from the fusion peptide or protein by methods known in the art. Fusion peptides or proteins can be cleaved using chemicals, such as cyanogen bromide, which cleaves at a methionine, or hydroxylamine, which cleaves between an asn and gly. Using standard recombinant DNA methodology, the nucleotide base pairs encoding these amino acids may be inserted just prior to the 5' end of the KGD or RGD-containing peptide or protein gene.

Alternatively, one can employ proteolytic cleavage of fusion peptides or proteins, which has been recently reviewed (Carter, P. (1990) in *Protein Purification: From Molecular Mechanisms to Large-Scale Processes*, Ladisch, M. R., Willson, R. C., Painton, C. C., and Builder, S. E., eds., American Chemical Society Symposium Series No. 427, Ch 13, 181–193).

Proteases such Factor Xa, thrombin, subtilisin and mutants, and a number of other have been successfully used to cleave fusion peptides or proteins. Typically, a peptide linker that is amenable to cleavage by the protease used is inserted between the "other" peptide or protein (e.g., the Z domain of peptide or protein A) and the KGD or RGD-containing peptide or protein of interest. Using recombinant DNA methodology, the nucleotide base pairs encoding the linker are inserted between the genes or gene fragments coding for the other peptides or proteins. Proteolytic cleavage of the partially purified fusion peptide or protein containing the correct linker can then be carried out on either the native fusion peptide or protein, or the reduced or denatured fusion peptide or protein.

The peptide or protein may or may not be properly folded when expressed as a fusion peptide or protein. Also, the specific peptide linker containing the cleavage site may or may not be accessible to the protease. These factors determine whether the fusion peptide or protein must be denatured and refolded, and if so, whether these procedures are employed before or after cleavage.

When denaturing and refolding are needed, typically the peptide or protein is treated with a chaotrope, such a guanidine HCl, and is then treated with a redox buffer, containing, for example, reduced and oxidized dithiothreitol or glutathione at the appropriate ratios, pH, and temperature, such that the peptide or protein of interest is refolded to its native structure.

General Chemical Synthetic Procedures

When peptides are not prepared using recombinant DNA technology, they are preferably prepared using solid-phase synthesis, such as that generally described by Merrifield, *J. Am. Chem. Soc.* (1963) 85, 2149, although other equivalent chemical syntheses known in the art are employable. Solid-phase synthesis is initiated from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a BHA resin or MBHA resin. The preparation of the hydroxymethyl resin is described by Bodansky et al., *Chem. Ind.* (London) (1966) 38,1597–1598. Chloromethylated resins are commercially available from BioRad Laboratories, Richmond, Calif. and from Lab. Systems, Inc. The preparation of such a resin is described by Stewart et al., "*Solid Phase Peptide Synthesis*" (Freeman & Co., San Francisco 1969), Chapter 1, pp. 1–6. BHA and MBHA resin supports are commercially available and are generally used only when the desired polypeptide being synthesized has an unsubstituted amide at the C-terminus.

The amino acids are coupled to the peptide chain using techniques well known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethylchloroformate, phenyl chloroformate, sec-butyl chloroformate, isobutyl chloroformate, pivaloyl chloride or like acid chlorides. Alternatively, the amino acid can be converted to an active ester such as a 2,4,5-trichlorophenyl ester, a pentachlorophenyl ester, a pentafluorophenyl ester, a p-nitrophenyl ester, a N-hydroxysuccinimide ester, or an ester formed from 1-hydroxybenzotriazole.

Another coupling method involves use of a suitable coupling agent such as N,N'-dicyclohexylcarbodiimide or N,N'-diisopropyl-carbodiimide. Other appropriate coupling agents, apparent to those skilled in the art, are disclosed in E. Gross & J. Meienhofer, *The Peptides: Analysis, Structure, Biology*, Vol. I: Major Methods of Peptide Bond Formation (Academic Press, N.Y., 1979).

It will be recognized that the α-amino group of each amino acid employed in the peptide synthesis must be protected during the coupling reaction to prevent side reactions involving their active α-amino function. It will also be recognized that certain amino acids contain reactive side-chain functional groups (e.g. sulfhydryl, amino, carboxyl, and hydroxyl) and that such functional groups must also be protected with suitable protecting groups to prevent a chemical reaction from occurring at that site during both the initial and subsequent coupling steps. Suitable protecting groups, known in the art, are described in E. Gross & J. Meienhofer, *The Peptides: Analysis, Structure, Biology*, Vol.3: Protection of Functional Groups in Peptide Synthesis (Academic Press, N.Y., 1981).

In the selection of a particular side-chain protecting group to be used in synthesizing the peptides, the following general rules are followed. An α-amino protecting group (a) must render the α-amino function inert under the conditions employed in the coupling reaction, (b) must be readily removable after the coupling reaction under conditions that will not remove side-chain protecting groups and will not alter the structure of the peptide fragment, and (c) must eliminate the possibility of racemization upon activation immediately prior to coupling. A side-chain protecting group (a) must render the side chain functional group inert under the conditions employed in the coupling reaction, (b) must be stable under the conditions employed in removing the α-amino protecting group, and (c) must be readily removable upon completion of the desired amino acid peptide under reaction conditions that will not alter the structure of the peptide chain.

It will be apparent to those skilled in the art that the protecting groups known to be useful for peptide synthesis will vary in reactivity with the agents employed for their removal. For example, certain protecting groups such as triphenylmethyl and 2-(p-biphenylyl)isopropyloxycarbonyl are very labile and can be cleaved under mild acid conditions. Other protecting groups, such as t-butyloxycarbonyl (BOC), t-amyloxycarbonyl. adamantyl-oxycarbonyl, and p-methoxybenzyloxycarbonyl are less labile and require moderately strong acids, such as trifluoroacetic, hydrochloric, or boron trifluoride in acetic acid, for their removal. Still other protecting groups, such as benzyloxycarbonyl (CBZ or Z), halobenzyloxycarbonyl, p-nitrobenzyloxycarbonyl cydoalkyloxycarbonyl, and isopropyloxycarbonyl, are even less labile and require stronger acids, such as hydrogen fluoride, hydrogen bromide, or boron trifluoroacetate in trifluoroacetic acid, for their removal. Among the classes of useful amino acid protecting groups are included:

(1) for an α-amino group, (a) aromatic urethane-type protecting groups, such as fluorenylmethyloxycarbonyl (FMOC) CBZ, and substituted CBZ, such as, e.g., p-chlorobenzyloxycarbonyl, p-6-nitrobenzyloxycarbonyl, p-bromobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (b) aliphatic urethane-type protecting groups, such as BOC, t-amyloxycarbonyl, isopropyloxycarbonyl, 2-(p-biphenylyl)-isopropyloxycarbonyl, allyloxycarbonyl and the like; (c) cycloalkyl urethane-type protecting groups, such as cyclopentyloxycarbonyl, adamantyloxycarbonyl, and cyclohexyloxycarbonyl; and d) allyloxycarbonyl. The preferred α-amino protecting groups are BOC or FMOC.

(2) for the side chain amino group present in Lys, protection maybe by any of the groups mentioned above in (1) such as BOC, p-chlorobenzyloxycarbonyl, etc.

(3) for the guanidino group of Arg, protection may be by nitro, tosyl, CBZ, adamantyloxycarbonyl, 2,2,5,7,8-pentamethylchroman-6-sulfonyl or 2,3,6-trimethyl-4-methoxyphenylsulfonyl, or BOC.

(4) for the hydroxyl group of Ser, Thr, or Tyr, protection maybe, for example, by $C_1$–$C_4$ alkyl, such as t-butyl; benzyl (BZL); substituted BZL, such as p-methoxybenzyl, p-nitrobenzyl, p-chlorobenzyl, o-chlorobenzyl, and 2,6-dichlorobenzyl.

(5) for the carboxyl group of Asp or Glu, protection may be, for example, by esterification using groups such as BZL, t-butyl, cyclohexyl, cyclopentyl, and the like.

(6) for the imidazole nitrogen of His, the tosyl moiety is suitably employed.

(7) for the phenolic hydroxyl group of Tyr, a protecting group such as tetrahydropyranyl, tert-butyl, trityl, BZL, chlorobenzyl, 4-bromobenzyl, and 2,6-dichlorobenzyl are suitably employed. The preferred protecting group is 2,6-dichlorobenzyl.

(8) for the side chain amino group of Asn or Gln, xanthyl (Xan) is preferably employed.

(9) for Met, the amino acid is preferably left unprotected.

(10) for the thio group of Cys, p-methoxybenzyl is typically employed.

The C-terminal amino acid, e.g., Lys, is protected at the N-amino position by an appropriately selected protecting group, in the case of Lys, BOC. The BOC-Lys-OH can be first coupled to the benzyhydrylamine or chloromethylated resin according to the procedure set forth in Horiki et al., *Chemistry Letters*, (1978)165–168 or using isopropylcarbodiimide at about 25° C. for 2 hours with stirring. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups are described in Schroder & Lubke, supra, (Chapter I, pp. 72–75).

After removal of the α-amino protecting group, the remaining α-amino and side-chain protected amino acids are coupled step within the desired order. As an alternative to adding each amino acid separately in the synthesis, some may be coupled to one another prior to addition to the solid-phase synthesizer. The selection of an appropriate coupling reage the skill of the art. Particularly suitable as a coupling reagent is N,N'-dicydohexylcarbodiimide or diisopropylcarbodiimide.

Each protected amino add or amino acid sequence is introduced into the solid-phase reactor in excess, and the coupling is suitably carried out in a medium of dimethylformamide (DMF) or $CH_2Cl_2$ or mixtures thereof. If incomplete coupling occurs, the coupling procedure is repeated before removal of the N-amino protecting group prior to the coupling of the next amino acid. The success of the coupling reaction at each stage of the synthesis may be monitored. A preferred method of monitoring the synthesis is by the ninhydrin reaction, as described by Kaiser et al., *Anal. Biochem*, 34:595 (1970). The coupling reactions can be performed automatically using well known methods, for example, a Biosearch 9500 Peptide Synthesizer.

Upon completion of the desired peptide sequence, the protected peptide must be cleaved from the resin support, and all protecting groups must be removed. The cleavage reaction and removal of the protecting groups is suitably accomplished simultaneously or stepwise. When the resin support is a chloro-methylated polystyrene resin, the bond anchoring the peptide to the resin is an ester linkage formed between the free carboxyl group of the C-terminal residue and one of the many chloromethyl groups present on the resin matrix. It will be appreciated that the anchoring bond can be cleaved by reagents that are known to be capable of breaking an ester linkage and of penetrating the resin matrix. One especially convenient method is by treatment with liquid anhydrous hydrogen fluoride. This reagent not only will cleave the peptide from the resin but also will remove all protecting groups. Hence, use of this reagent will directly afford the fully deprotected peptide. When the chloromethylated resin is used hydrogen fluoride treatment results in the formation of the free peptide adds. When the benzhydrylamine resin is used, hydrogen fluoride treatment results directly in the free peptide amines. Reaction with hydrogen fluoride in the presence of anisole and dimethylsulfide at 0° C. for one hour will simultaneously remove the side-chain protecting groups and release the peptide from the resin.

When it is desired to cleave the peptide without removing protecting groups, the protected peptide-resin can undergo methanolysis to yield the protected peptide in which the C-terminal carboxyl group is methylated. The methyl ester is then hydrolyzed under mild alkaline conditions to give the free C-terminal carboxyl group. The protecting groups on the peptide chain then are removed by treatment with a strong acid, such as liquid hydrogen fluoride. A particularly useful technique for methanolysis is that of Moore et al., *Peptides, Proc. Fifth Amer. Pept. Symp.*, M. Goodman and J. Meienhofer, Eds., (John Wiley, N.Y., 1977), p. 518–521, in which the protected peptide-resin is treated with methanol and potassium cyanide in the presence of crown ether.

Another method for cleaving the protected peptide from the resin when the chloromethylated resin is employed is by ammonolysis or by treatment with hydrazine. If desired, the resulting C-terminal amide or hydrazide can be hydrolyzed to the free C-terminal carboxyl moiety, and the protecting groups can be removed conventionally.

It will also be recognized that the protecting group present on the N-terminal α-amino group may be removed preferentially either before or after the protected peptide is cleaved from the support.

Purification of the polypeptides of the invention is typically achieved using conventional procedures such as preparative HPLC (including reversed phase HPLC) or other known chromatographic techniques such as gel permeation, ion exchange, partition chromatography, affinity chromatography (including monoclonal antibody columns) or countercurrent distribution.

Polypeptide chains are polymerized by crosslinking monomer chains with polyfunctional crosslinking agents, including compound 1, either directly or indirectly through multifunctional polymers. Ordinarily, two substantially identical polypeptides are crosslinked at their C or N termini using a bifunctional crosslinking agent. The agent is used to crosslink the terminal amino and/or carboxyl groups. Generally, both terminal carboxyl groups or both terminal amino groups are crosslinked to one another, although by selection of the appropriate crosslinking agent the alpha amino of one polypeptide is crosslinked to the terminal carboxyl group of the other polypeptide. Preferably, the polypeptides are substituted at their C-termini with cysteine. Under conditions well known in the art a disulfide bond can be formed between the terminal cysteines, thereby crosslinking the polypeptide chains. For example, disulfide bridges are conveniently formed by metal-catalyzed oxidation of the free cysteines or by nucleophilic substitution of a suitably modified cysteine residue. Selection of the crosslinking agent will depend upon the identities of there active side chains of the amino acids present in the polypeptides. For example, disulfide crosslinking would not be preferred if cysteine was present in the polypeptide at additional sites other than the C-terminus. Also within the scope hereof are peptides crosslinked with methylene bridges.

Suitable crosslinking sites on the peptides, aside from the N-terminal amino and C-terminal carboxyl groups, include epsilon amino groups found on lysine residues, as well as amino, imino, carboxyl, sulfhydryl and hydroxyl groups located on the side chains of internal residues of the peptides or residues introduced into flanking sequences. Crosslinking through externally added crosslinking agents is suitably achieved, e.g., using any of a number of reagents familiar to those skilled in the art, for example, via carbodiimide treatment of the polypeptide. Other examples of suitable multifunctional (ordinarily bifunctional) crosslinking agents include 1,1-bis(diazoacetyl)- 2-phenylethane; glutaraldehyde; N-hydroxysuccinimide esters (Bragg and Hou, *Arch. Biochem. Biophys.* (1975) 167, 311–321; Anjaneyla and Staros, *Int. J. Pep. Pro. Res.* (1987)30, 117–124), such as esters with 4-azidosalicylic acid; homobifunctional imidoesters including disuccinimidyl esters such as 3,3'-dithiobis (succinimidyl-propionate) and dimethyladipimidate dihydrochloride (Zahn, *Agnew. Chem.* (1955)67, 561–572; Golden and Harrison, *Biochemistry* (1982)21, 3862–3866); bifunctional maleimides such as bis-N-maleimido-1,8-octane; disuccinimidyl suberate (Novick et al., *J. Biol. Chem.* (1987) 262, 8483–8487), bis(sulfosuccinimidyl) suberate (Lee and Conrad, *J. Immunol.* (1985) 134 518–525); heterobifunctional crosslinking reagents (Lomants and Fairbanks, *Arch. Biochem. Biophys.* (1976)167, 311–321; Anjaneyuia and Staros, supra; Partis et al., *J. Pro. Chem.* (1983)2, 263–277; Weltman et al., *Bio Techniques*, (1983)1, 148–152; Yoshtake et al., *J. Biochem.* (1982) 92, 1423–1424), including those with an N-hydroxysuccinimide moiety at one end and a maleimido group on the other end; succinimidyl 4-(N-maleimidomethyl) cyclohexane- 1-carboxylate (SMCC) (Mahan et al. *Anal. Biochem.* (1987)162, 163–170); sulfo-SMCC (Hashida et al., *J. Applied Biochem.* (1984) 6, 56–63); m-maleimidobenzoyl-N-hydroxysuccinimide ester (MBS); sulfo-MBS; succinimidyl 4-(p-maleimidophenyl) butyrate (SMPB); sulfo-SMPB; N-succinimidyl(4-iodoacetyl)aminobenzoate (SLAB); sulfo-SIAB; 1-ethyl-3-(3-dimethylaminopropyl)carbodiimide hydrochloride (EDC); and N-hydroxysulfosuccinimide. Crosslinking agents such as methyl- 3-[(p-azido-phenyl)dithio] propioimidate yield photoactivatable intermediates which are capable of forming crosslinks in the presence of light. If necessary, sensitive residues such as the side chains of the diargininyl group are protected during crosslinking and the protecting groups removed thereafter.

Polymers capable of multiple crosslinking serve as indirect crosslinking agents. For example, cyanogen bromide activated carbohydrates and the systems described in U.S. Pat. Nos. 3,959,080; 3,969,287; 3,691,016; 4,195,128; 4,247,642; 4,229,537; 4,055,635 and 4,330,440 are suitably modified for crosslinking the peptides herein. Crosslinking to amino groups of the peptides is accomplished by known chemistries based upon cyanuric chloride, carbonyl diimidazole, aidehyde reactive groups (PEG aikoxide plus diethyl acetal of bromoacetaldehyde; PEG plus DMSO and acetic anhydride, or PEG chloride plus the phenoxide of 4-hydroxybenzaldehyde). Also useful are succinimidyl active esters, activated dithiocarbonate PEG, and 2,4,5-trichlorophenyl-chloroformate- or p-nitrophenyl-chloroformate-activated PEG. Carboxyl groups are derivatized by coupling PEG-amine using carbodiimide. Ordinarily, however, the crosslinking agent is not a multifunctional polymer but instead is a small molecule being less than about 500 in MW.

The peptides of this invention also may be conformationally stabilized by cyclization. The peptides ordinarily are cyclized by covalently bonding the N and C-terminal domains of one peptide to the corresponding domain of another peptide of this invention so as to form cydooligomers containing two or more iterated peptide sequences, each internal peptide having substantially the same sequence. Further, cydized peptides (whether cyclooligomers or cylcomonomers) are crosslinked to form 1-3 cyclic structures having from 2 to 6 peptides comprised therein. The peptides preferably are not covalently bonded through α-amino and main chain carboxyl groups (head to tail), but rather are cross-linked through the side chains of residues located in the N and C-terminal domains. The linking sites thus generally will be between the side chains of the residues.

The cyclic structures of the present invention will have the general formula:

wherein A and B represent the peptides of this invention and are the same or different. A and B are single peptides or head-to-tail polymers of two or more such peptides. C represents one or more bonds or crosslinking moieties.

Many suitable methods per se are known for preparing mono-or poly-cyclized peptides as contemplated herein. Lys/Asp cydization has been accomplished using N-α-Boc-amino acids on solid-phase support with Fmoc/9-fluorenyl-methyl (OFm) side-chain protection for Lys/Asp; the process is completed by piperidine treatment followed by cyclization.

Glu and Lys side chains also have been crosslinked in preparing cyclic or bicydic peptides: the peptide is synthesized by solid phase chemistry on a p-methylbenzhydry-lamine resin. The peptide is cleaved from the resin and deprotected. The cyclic peptide is formed using diphenylphosphorylazide in diluted methylformamide. For an alternative procedure, see Schiller et al., *Peptide Protein Res.* (1985) 25, 171–177. See also U.S. Pat. No. 4,547,489.

Disulfide crosslinked or cyclized peptides are generated by conventional methods. The method of Pelton et al., (*J. Med. Chem.* (1986) 29, 2370–2375) is suitable, except that a greater proportion of cyclooligomers are produced by conducting there action in more concentrated solutions than the dilute reaction mixture described by Pelton et al., for the production of cylomonomers. The same chemistry is useful for synthesis of dimers or cyclooligomers or cyclomonomers. Also useful are thiomethylene bridges (*Tetrahedron Letters* (1984) 25, 2067–2068). See also Cody et al., *J. Med. Chem.* (1985) 28, 583.

The preferred thioether sulfoxide, and sulfone cyclization method employed in this invention is described in WO 91/01331, published 7 Feb. 1991.

The desired cyclic or polymeric peptides are purified by gel filtration followed by reversed-phase high pressure liquid chromatography or other conventional procedures. The peptides are sterile filtered and formulated into conventional pharmacologically acceptable vehicles.

The compounds described in this invention may be isolated as the free acid or base or converted to salts of various inorganic and organic acids and bases. Such salts are within the scope of this invention. Examples of such salts include ammonium, metal salts like sodium, potassium, calcium and magnesium; salts with organic bases like dicyclohexylamine, N-methyl-D-glucamine and the like; and salts with amino acids like arginine or lysine. Salts with inorganic and organic acids may be likewise prepared, for example, using hydrochloric, hydrobromic, sulfuric, phosphoric, trifluoroacetic, methanesulfonic, malic, maleic, fumaric and the like. Non-toxic and physiologically compatible salts are particularly useful although other less desirable salts may have use in the processes of isolation and purification.

A number of methods are useful for the preparation of the salts described above and are known to those skilled in the art. For example, reaction of the free acid or free base form of a compound of Formula I with one or more molar equivalents of the desired acid or base in a solvent or solvent mixture in which the salt is insoluble; or in a solvent like water after which the solvent is removed by evaporation, distillation or freeze drying. Alternatively, the free acid or base form of the product may be passed over an ion exchange resin to. form the desired salt or one salt form of the product may be converted to another using the same general process.

Use of Inhibitors

As previously indicated, many common human disorders are characteristically associated with a hypercoagulable state leading to intravascular thrombi and emboli. These are a major cause of medical morbidity, leading to phlebitis, infarction, and stroke, and of mortality, from stroke and pulmonary and cardiac emboli. A large percentage of such patients have no antecedent risk factors, and develop venous thrombophlebitis and subsequent pulmonary emboli without a known cause. Other patients who form venous thrombi have underlying diseases known to predispose to these syndromes.

Some of these patients may have genetic or acquired deficiencies of factors that normally prevent hypercoagulability, such as anti-thrombin 3. Others have mechanical obstructions to venous flow, such as tumor masses, that lead to low flow states and thrombosis. Patients with malignancy have a high incidence of thrombotic phenomena, for unclear reasons. Antithrombotic therapy in this situation with currently available agents is dangerous and often ineffective.

Alternatively, the platelet aggregation inhibitors of this invention may be used in a pharmaceutical composition, optionally with a thrombolytic agent or anticoagulant to treat a mammal usually having an increased propensity for thrombus formation. Representative thrombolytic agents include but are not limited to; tissue plasminogen activator (t-PA), streptokinase, acylated plasminogen/streptokinase activator complex (APSAC), urokinase, Pro-urokinase (suc-PA), and the like. Representative anticoagulants include but are not limited to heparin, dicumarol, warfin, hirudin, and the like (see e.g., Colman, et al., *Hemostasis and Thrombosis*, 2nd Edition, J. B. Lippincott Co., Philadelphia (1987)).

Patients with atherosclerosis are predisposed to arterial thromboembolic phenomena for a variety of reasons. Atherosclerotic plaques from niduses form platelet plugs and thrombi that lead to vascular narrowing and occlusion, resulting in myocardial and cerebral ischemic disease. Thrombi that break off and are released into the circulation can cause infarction of different organs, especially the brain, extremities, heart and kidneys. After myocardial infarctions, clots can form in weak, poorly functioning cardiac chambers and be released into the circulation to cause emboli. All such patients with atrial fibrillation are felt to be at great risk for stroke and require antithrombotic therapy.

In addition, thrombolytic therapy for acute myocardial infarction has become an established procedure for patients (Collen, D. and Stump, D. (1988) *Ann Rev Med* 39, 405–423). However, currently available thrombolytic agents are not effective in all patients which is manifest by reocclusion, resistance to reperfusion, prolonged times to achieve normal coronary flow and the like. Since platelet mediated thrombosis is a major mechanism involved in the efficacy of thrombolytic therapy, agents which can be used to affect platelet aggregation in adjunctive therapy to treat acute myocardial infarction would have significant beneficial effects. Suitable thrombolytic agents include: tissue plasminogen activator, streptokinase, urokinase, prourokinase, and modifications thereof.

Patients whose blood flows over artificial surfaces, such as prosthetic synthetic cardiac valves or through extracorporeal perfusion devices, are also at risk for the development of platelet plugs, thrombi, and emboli. It is standard practice that patients with artificial cardiac valves be chronically anti-coagulated.

Thus, a large category of patients, including those with cancer, atherosclerosis, coronary artery disease, artificial heart valves, and a history of stroke, phlebitis, or pulmonary emboli, are candidates for limited or chronic antithrombotic therapy. However, this therapy is often ineffective or morbid in its own right. This is partially because the number of available therapeutic agents is limited and these, for the most part, act by reducing levels of circulating clotting factors. These agents are, therefore, not necessarily aimed at the patient's underlying hematologic problem, which often concerns an increased propensity for platelet aggregation and adhesion. They also cause the patient to be very susceptible to abnormal bleeding. Available antiplatelet agents, such as aspirin, inhibit the cyclooxygenase-induced activation of platelets only and are often inadequate for therapy.

In the management of thromboembolic disorders the compounds of this invention may be utilized in compositions such as tablets, capsules or elixers for oral administration; suppositories for rectal administration; sterile solutions or suspensions for injectable administration, atomized droplets for pulmonary or nasal administration, and the like. Animals in need of treatment using compounds of this invention can be administered dosages that will provide optimal efficacy. The dose and method of administration will vary from animal to animal and be dependent upon such factors as weight, diet, concurrent medication and other factors which those skilled in the medical arts will recognize.

Dosage Formulations

Dosage formulations of the cyclic polypeptides of the present invention are prepared for storage or administration by mixing the cyclic polypeptide having the desired degree of purity with physiologically acceptable carriers, excipients, or stabilizers. Such materials are non-toxic to the recipients at the dosages and concentrations employed, and include buffers such as phosphate, citrate, acetate and other organic add salts; antioxidants such as ascorbic acid; low molecular weight (less than about ten residues) peptides such as polyarginine, proteins, such as serum albumin, gelatin, or immunoglobulins; hydrophilic polymers such as polyvinylpyrrolidinone; amino adds such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sobitol; counterions such as sodium and/or nonionic surfactants such as Tween, Pluronics or polyethyleneglycol.

Dosage formulations of the cyclic polypeptides of the present invention to be used for therapeutic administration must be sterile. Sterility is readily accomplished by filtration through sterile filtration membranes such as 0.2 micron membranes. Cyclic polypeptide formulations ordinarily will be stored in lyophilized form or as an aqueous solution. The pH of the cyclic polypeptide preparations typically will be between 3 and 11, more preferably from 5 to 9 and most preferably from 7 to 8. It will be understood that use of certain of the foregoing excipients, carriers, or stabilizers will result in the formation of cyclic polypeptide salts. While the preferred route of administration is by hypodermic injection needle, other methods of administration are also anticipated such as suppositories, aerosols, oral dosage formulations and topical formulations such as ointments, drops and dermal patches.

Therapeutic cyclic polypeptide formulations generally are placed into a container having a sterile access port, for example, an intravenous solution bag or vial having a stopper pierceable by hypodermic injection needle.

Therapeutically effective dosages may be determined by either in vitro or in vivo methods. One method of evaluating therapeutically effective dosages consists of taking the cyclic polypeptide cyclo-S-acetyl-dTyr-Lys-Gly-Asp-Cys-Lys-NH$_2$ and determining a 50% inhibitory concentration (IC$_{50}$) of inhibiting fibrinogen binding to the GP II$_b$ III$_a$ platelet receptor. Similarly, in a platelet aggregation assay using the same cyclic peptide, the IC$_{50}$ is measured. Based upon such in vitro assay techniques, a therapeutically effective dosage range may be determined. For each particular cyclic polypeptide of the present invention, individual determinations may be made to determine the optimal dosage required. The range of therapeutically effective dosages will naturally be influenced by the route of administration. For injection by hypodermic needle it may be assumed the dosage is delivered into the body's fluids. For other routes of administration, the absorption efficiency must be individually determined for each cyclic polypeptide by methods well known in pharmacology.

The range of therapeutic dosages is from about 0.001 nM to 1.0 mM, more preferably from 0.1 nM to 100 µM, and most preferably from 1.0 nM to 50 µM.

Typical formulation of compounds of Formula I as pharmaceutical compositions are discussed below.

About 0.5 to 500 mg of a compound or mixture of compounds of Formula I, as the free acid or base form or as a pharmaceutically acceptable salt, is compounded with a physiologically acceptable vehicle, carrier, excipient, binder, preservative, stabilizer, flavor, etc., as called for by accepted pharmaceutical practice. The amount of active ingredient in these compositions is such that a suitable dosage in the range indicated is obtained.

Typical adjuvants which may be incorporated into tablets, capsules and the like are a binder such as acacia, corn starch or gelatin; an excipient such as microcrystalline cellulose; a disintegrating agent like corn starch or alginic acid; a lubricant such as magnesium stearate; a sweetening agent such as sucrose or lactose; a flavoring agent such as peppermint, wintergreen or cherry. When the dosage form is a capsule, in addition to the above materials it may also contain a liquid carrier such as a fatty oil. Other materials of various types may be used as coatings or as modifiers of the physical form of the dosage unit. A syrup or elixir may contain the active compound, a sweetener such as sucrose, preservatives like propyl paraben, a coloring agent and a flavoring agent such as cherry. Sterile compositions for injection can be formulated according to conventional pharmaceutical practice. For example, dissolution or suspension of the active compound in a vehicle such as water or naturally occurring vegetable oil like sesame, peanut, or cottonseed oil or a synthetic fatty vehicle like ethyl oleate or the like may be desired. Buffers, preservatives, antioxidants and the like can be incorporated according to accepted pharmaceutical practice.

The present invention has of necessity been discussed herein by reference to certain specific methods and materials. It is to be understood that the discussion of these specific methods and materials in no way constitutes any limitation on the scope of the present invention, which extends to any and all alternative materials and methods suitable for accomplishing the objectives of the present invention.

All references cited herein are expressly incorporated herein by reference.

EXAMPLES

In the following Examples, common α-amino acids may be described by the standard three letter amino acid code when referring to intermediates and final products. When the three-letter code begins with a lower-case letter, it is understood the amino acid is unnatural or the D-isomeric form. Standard abbreviations are listed in The Merck Index, 10th Edition, pp Misc-2- Misc-3. Modified or unusual α-amino acids such as norleucine (Nle) and ornithine (Orn) are designated as described in U.S. Patent and Trademark Office Official Gazette 1114TMOG, May 15, 1990. If the product or intermediate name is preceded by "cyclo-S-" this shall be taken to mean that the peptide has been cyclized through a sulfur atom.

EXAMPLE 1

Bleeding Time and EX-Vivo Platelet Aggregation Rabbit Model

A. Animal Preparation and Blood Sampling

Unanesthetized male New Zealand White rabbits (2.5–3.5 kg) are placed in a standard rabbit restrainer. Ears are shaved and a 20 G Teflon catheter with flowswitch (Viggo) is placed in the medial artery, flushed with saline and locked with 1 ml of heparinized saline (10 m/ml). A 22 G catheter (Abbott) fitted with an injection cap (Medex) is placed in the marginal vein of the same ear. Saline or a GP $II_bIII_a$ receptor antagonist, at a concentration of 1 to 3 mg/ml, is infused via the venous catheter. At time 0, 41% of the dose is given as a bolus over 2 minutes. The remainder is continuously infused over the following 60 minutes. Blood samples (3.2 ml) are collected into syringes without needles via the arterial catheter at −10, −5, 10, 45, and 60 minutes. The first 0.5 ml is discarded and the following 2.7 ml is collected directly into a syringe containing 0.3 ml of 3.8% sodium citrate. The sample is divided into 1.5 ml aliquots and centrifuged at room temperature for 5 seconds at 12,000 G. The resulting platelet rich plasma (PRP) is used to measure ex-vivo platelet aggregation (XPA). At −10 and 60 minutes an additional 1 cml sample is drawn for an automated blood count (Baker instruments). Catheters are flushed and locked after every sample.

B. Ex-Vivo Platelet Aggregation (XPA)

300 ml of PRP is placed in a disposable glass cuvette with a stir bar. The cuvette is placed in the temperature regulated light path of a light transmittance aggregometer (Chronolog) and equilibrated to a 37° C. Baseline transmittance is recorded for 30 seconds, after which 10 ml of ADP (1 mM) is added and the change in transmittance recorded. The maximum change from baseline (dT) is noted for each sample. The extent of inhibition of XPA that is produced by an inhibitor is calculated for each animal as follows: Mean dTs are calculated for the pre and post infusion values, and then, percent inhibition is calculated as (1-dt (post)/ddt (pre))×100.

C. Cutaneous Bleedins Times (CBT)

CBT is measured at −10, −5, 10, and 45 minutes on the opposite ear, using an automated incision-making instrument (Surgicutt®, ITD). An incision (5mm×1 mm deep) is made on the dorsal surface of the ear at sites not supplied by major blood vessels. Blood is blotted away with absorbent paper placed near the incision site, every 2 to 15 seconds, to a maximum of 15 minutes. Cessation of bleeding is defined as no blood forming at the incision site for 15 seconds. The range of duplicate CBT in 40 normal rabbits was 0.88 to 3.38 minutes.

D. Peripheral Blood Flow (PBF)

For the experiments summarized in Table 1, PBF was monitored by observation of the condition of the blood vessels in the rabbits' ears, prior to and during the infusion. Normal flow is defined as ears that appear pink to red, with no visible constriction of the major blood vessels. Decreased flow applies to ears that have constricted vessels resulting in cold, pallid ears for up to 40 minutes following the start of the inhibitor infusion.

TABLE 1

Rabbit Cutaneous Bleeding Time, Peripheral Blood Flow v. Ex Vivo Platelet Aggregation and Inhibitor Dose

| Compound[1] | Dose (mg/kg)[2] | CBT (post/pre)[3] | XPA (% Inhib)[4] | PBF[5] | Number of Samples Tested |
|---|---|---|---|---|---|
| Control | Saline | 1.09 | 11 | NORMAL | 2 |
| 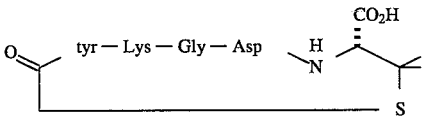 | 1.5 + 0.036 | 8.57 | 96 | NORMAL | 1 |
| 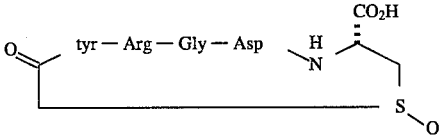 | 0.013 + 0.0003 | 2.74 | 55 | NORMAL | 1 |
| 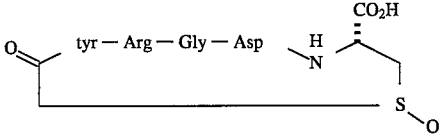 | .375 + 0.009 | 5.67 | 95 | NORMAL | 1 |

TABLE 1-continued

Rabbit Cutaneous Bleeding Time, Peripheral Blood Flow v. Ex Vivo Platelet Aggregation and Inhibitor Dose

| Compound[1] | Dose (mg/kg)[2] | CBT (post/pre)[3] | XPA (% Inhib)[4] | PBF[5] | Number of Samples Tested |
|---|---|---|---|---|---|
| tyr—Arg—Gly—Asp—[cyclic with CO₂H, H-N, S=O side chain] | 0.5 + 0.012 | 8.77 | 99 | NORMAL | 2 |
| tyr—Lys—Gly—Asp—[cyclic with CO₂H, H-N, phenyl side chain] | 1.5 + 0.036 | 4.47 | 94 | NORMAL | 2 |
| tyr—Arg—Gly—Asp— Cys—Arg—NH₂ [cyclic via S] | 0.5 + 0.012 | 1.71 | 100 | NORMAL | 1 |
| tyr—Arg—Gly—Asp— Cys—Arg—NH₂ [cyclic via S] | 1.5 + 0.036 | 6.72 | 95 | NORMAL | 2 |
| tyr—Arg—Gly—Asp— Cys—Lys—NH₂ [cyclic via S] | 1.5 + 0.036 | 1.95 | 97 | NORMAL | 2 |
| tyr—Arg—Gly—Asp— Cys—Orn—NH₂ [cyclic via S] | 1.5 + 0.036 | 1.26 | 100 | NORMAL | 2 |
| tyr—Arg—Gly—Asp— Cys—orn—NH₂ [cyclic via S] | 1.5 + 0.036 | 1.40 | 53 | NORMAL | 1 |
| tyr—Arg—Gly—Asp— Cys—Tyr—Arg—NH₂ [cyclic via S] | 1.5 + 0.036 | 4.10 | 98 | NORMAL | 2 |
| tyr—Arg—Gly—Asp—[cyclic with CO₂H, H-N, guanidino side chain] | 1.5 + 0.036 | 1.46 | 55 | NORMAL | 1 |
| tyr—Arg—Gly—Asp—[cyclic with CO₂H, H-N, guanidino side chain] | 1.5 + 0.036 | 1.00 | 1 | NORMAL | 1 |

TABLE 1-continued

Rabbit Cutaneous Bleeding Time, Peripheral Blood Flow v. Ex Vivo Platelet Aggregation and Inhibitor Dose

| Compound[1] | Dose (mg/kg)[2] | CBT (post/pre)[3] | XPA (% Inhib)[4] | PBF[5] | Number of Samples Tested |
|---|---|---|---|---|---|
| *structure: tyr—Arg—Gly—Asp with CO₂H, NH₂, S* | 1.5 + 0.036 | 8.17 | 100 | NORMAL | 1 |
| *structure: tyr—Arg—Gly—Asp with CO₂H, NH₂, S* | 1.5 + 0.036 | 1.42 | 35 | NORMAL | 2 |
| *structure: H₂N—chain, tyr—Arg—Gly—Asp, S* | 1.5 + 0.036 | 0.94 | 96 | NORMAL | 1 |
| *structure: H₂N—chain, tyr—Arg—Gly—Asp, S* | 1.5 + 0.036 | 1.13 | 98 | NORMAL | 1 |
| *structure: tyr—Lys—Gly—Asp, Arg—NH₂, S* | 1.5 + 0.036 | 3.29 | 100 | NORMAL | 1 |
| *structure: tyr—Lys—Gly—Asp, Lys—NH₂, S* | 1.5 + 0.036 | 1.13 | 100 | NORMAL | 1 |
| *structure: tyr—Arg—Gly—Asp, Arg—NH₂* | 1.5 + 0.036 | 7.98 | 98 | NORMAL | 1 |
| *structure: tyr—Arg—Gly—Asp, Lys—NH₂* | 1.5 + 0.036 | 10.00 | 99 | NORMAL | 1 |

TABLE 1-continued

Rabbit Cutaneous Bleeding Time, Peripheral Blood Flow v. Ex Vivo Platelet Aggregation and Inhibitor Dose

| Compound[1] | Dose (mg/kg)[2] | CBT (post/pre)[3] | XPA (% Inhib)[4] | PBF[5] | Number of Samples Tested |
|---|---|---|---|---|---|
| 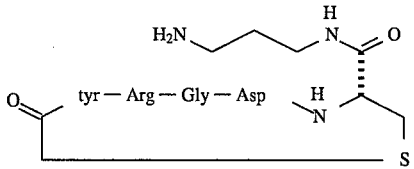 | 1.5 + 0.036 | 1.27 | 99 | NORMAL | 1 |
| 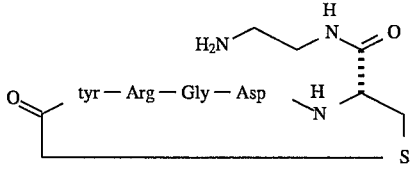 | 1.5 + 0.036 | 0.81 | 88 | NORMAL | 1 |
| 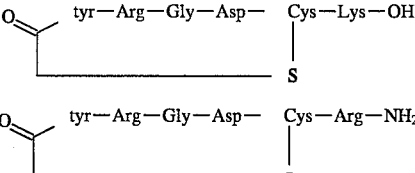 tyr—Arg—Gly—Asp— Cys—Lys—OH \| S | 1.5 + 0.036 | 6.14 | 100 | NORMAL | 1 |
|  tyr—Arg—Gly—Asp— Cys—Arg—NH$_2$ \| S—O | 0.5 + 0.012 | 3.90 | 100 | NORMAL | 1 |
| 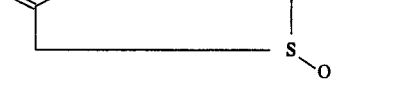 tyr—Arg—Gly—Asp— Cys—Arg—NH$_2$ \| S—O | 1.5 + 0.036 | 16.67 | 95 | NORMAL | 1 |
| 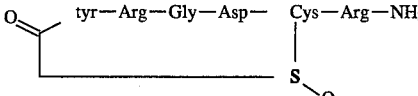 tyr—Arg—Gly—Asp— Cys—Arg—NH$_2$ \| S—O | 1.5 + 0.036 | 1.17 | 99 | NORMAL | 1 |
| 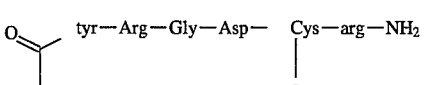 tyr—Arg—Gly—Asp— Cys—arg—NH$_2$ \| S—O | 1.5 + 0.036 | 0.93 | 64 | NORMAL | 1 |
| 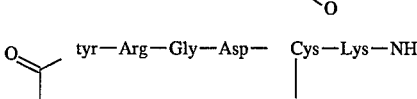 tyr—Arg—Gly—Asp— Cys—Lys—NH$_2$ \| S—O  3-bromyl tyrosine | 1.5 + 0.036 | 0.77 | 91 | NORMAL | 1 |
| 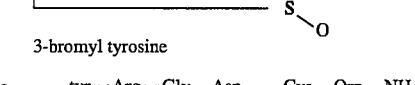 tyr—Arg—Gly—Asp— Cys—Orn—NH$_2$ \| S—O | 1.5 + 0.036 | 2.63 | 99 | NORMAL | 1 |
| 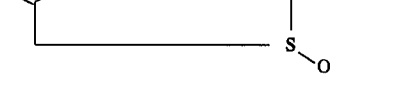 tyr—Arg—Gly—Asp— Cys—Orn—NH$_2$ \| S—O | 1.5 + 0.036 | 1.09 | 71 | NORMAL | 1 |
| 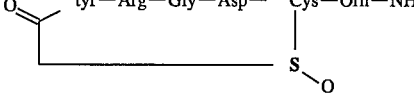 tyr—Arg—Gly—Asp— Cys—orn—NH$_2$ \| S—O | 1.5 + 0.036 | 1.50 | 98 | NORMAL | 1 |

TABLE 1-continued

Rabbit Cutaneous Bleeding Time, Peripheral Blood Flow v. Ex Vivo Platelet Aggregation and Inhibitor Dose

| Compound[1] | Dose (mg/kg)[2] | CBT (post/pre)[3] | XPA (% Inhib)[4] | PBF[5] | Number of Samples Tested |
|---|---|---|---|---|---|
| 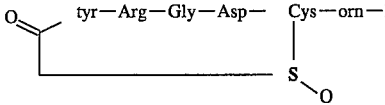 tyr—Arg—Gly—Asp—Cys—orn—NH$_2$ (cyclic with S—O) | 1.5 + 0.036 | 1.14 | 41 | NORMAL | 1 |
| 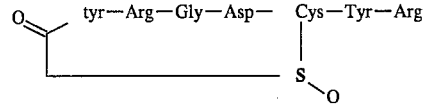 tyr—Arg—Gly—Asp—Cys—Tyr—Arg—NH$_2$ (cyclic with S—O) | 1.5 + 0.036 | 1.18 | 52 | NORMAL | 1 |

[1]Structure using three-letter code for amino acids; capital letters indicate L-configuration, lower case indicates D-configuration.
[2]Dose = Bolus dose in mg/kg; the additional amount indicated (also in mg/kg) was given by continuous infusion over 60 minutes.
[3]CBT = Cutaneous bleeding time in a ratio of an average of the post infusion bleeding times divided by the average of the pre bleeding times.
[4]XPA = Ex vivo platelet aggregation given in % inhibition of platelet aggregation.
[5]PBF = Peripheral blood flow in arbitrary units and is measured visually.

In an alternative series of experiments, (Table 2) PBF was measured quantitatively with a laser Doppler flow probe (Perimed). The probe was positioned securely over the vascular bed of one ear and flow monitored continuously. Each inhibitor was infused and CBT measured in the opposing ear. No arterial catheter was placed for blood sampling, consequently XPA was not measured in these animals. However, the doses used were shown in previous experiments to effectively inhibit XPA.

CBT, XPA, and observed PBF are summarized in Table 1. The ratio of the post to pre treatment CBT was calculated for each animal by dividing the mean of the 2 post-treatment samples by the mean of the pre samples. In two saline control rabbits the mean±sd ratio of post treatment CBT (n=10) to a mean pre-treatment CBT was 1.12±0.19.

TABLE 2

Rabbit Peripheral Blood Flow measured by Doppler laser

| Compound[1] | Time (Min)[2] | CBT (min)[3] | PBF (units)[4] |
|---|---|---|---|
| 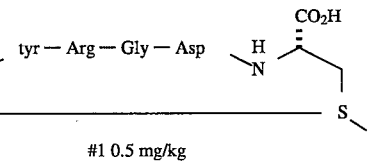 tyr—Arg—Gly—Asp—(CO$_2$H, H, N)—S—O #1 0.5 mg/kg | 0<br>10<br>45 | 1.2<br>15.0 | 211<br>220 |
| 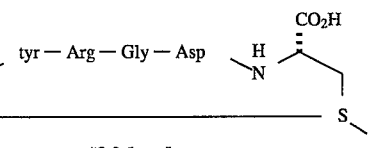 tyr—Arg—Gly—Asp—(CO$_2$H, H, N)—S—O #2 0.5 mg/kg | 0<br>10<br>45 | 2.5<br>15.0<br>15.0 | 395<br>380<br>356 |
| 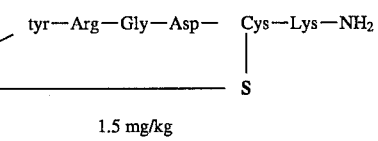 tyr—Arg—Gly—Asp—Cys—Lys—NH$_2$ (cyclic S) 1.5 mg/kg | 0<br>10<br>45 | 1.4<br>1.8<br>2.0 | 304<br>283<br>338 |

[1]Structure using three-letter code for amino acids; capital letters indicate L-configuration, lower case indicates D-configuration.
[2]Time of sampling.
[3]CBT = Cutaneous bleeding time in a ratio of an average of the post infusion bleeding times divided by the average of the pre bleeding times.
[4]PBF = Peripheral blood flow in arbitrary units and is measured using a laser doppler flow probe.

E. Results

The experiments measuring PBF by laser doppler probe are summarized in Table 2. As a positive control, epinephrine was infused intravenously (1 mg over 2 minutes.) at 60 minutes. The resulting vasoconstriction reduced flow to near 0 flow units within 5 minutes.

The doses listed in the Tables refer to the bolus portion only. There were no significant changes in any of the blood indices measured.

EXAMPLE 2

Fibrinogen-GP $II_bIII_a$ Receptor ELISA Binding Assay

The method used is essentially that described in Nachman and Leung (*J. Clin. Invest.*, 69:263–269 [1982]). The GP $II_bIII_a$ is essentially purified as described in Fitzgerald et al., (*Anal. Biochem.* 151:169–177 [1985]).

A. GP $II_bIII_a$ Purification

Outdated human platelets are washed 3 times with 10 mM tris-HCl, 150 mM NaCl (TBS), 1 mM EDTA, pH 7.5, and centrifuged at 2000×g to pellet cells. Cells are lysed in 5 pellet volumes of TBS, 1% Triton X-100, 1 mM $Ca_2Cl_2$, and followed by centrifugation at 30,000×g. The supernatant fraction is collected and the supernatant is loaded onto a concanavalin-A column, previously equilibrated in TBS, 1 mM $Ca_2Cl_2$, 0.1% Triton, 0.05% $NaN_3$ and eluted with 0.2M α-methylmannoside. Fractions are pooled and loaded onto a heparin-agarose column. The flowthrough is collected and concentration on an Amicon YM 30 filter to a volume of approximately 5–10 mi. The concentrate is then applied to an S-300 column (500 ml) and 6 ml fractions are collected. The GP $II_bIII_a$ containing fractions are collected, pooled, and stored at –80° C.

B. Purification of Low Solubility Fraction of Fibrinogen

The purification of fibrinogen is conducted essentially as described by Lipinska et al., (*J. Lab. Clin. Med.* 507, [1974]). Briefly, a 0.3% w/v solution of human fibrinogen (Kabi #5302) is dissolved in 150 mM NaCl. Saturated $(NH_4)_2SO_4$ is added dropwise with stirring to the fibrinogen solution to obtain about 16% saturation. The precipitate is spun down in appropriate size bottles at 2000×g. The supernatant is decanted and the precipitate resuspended in 150 mM NaCl (approximately 50% of the original volume). $NH_4SO_4$ is again added dropwise to obtain 16% saturation. The suspension is spun down and the precipitate is resuspended in Tris-saline in a minimal volume (approximately 5% of the original volume). Any remaining insoluble material is spun down at 2000 rpm in a Sorval type centrifuge and the fibrinogen supernatant is decanted and dialyzed overnight at 4° C. against Tris-saline. Characterization of the fibrinogen is by the Bradford protein assay, SDS-PAGE, and/or Western blotting using well known standard procedures.

C. ELISA Assay

Briefly, 96 well plates are coated (Type Nunc 1 Maxisorp™) with 10 µg/ml purified fibrinogen (100 µl/well), and allowed to stand overnight at 4° C. The plates are washed three times with PBS Tween (0.137M NaCl, 0.003 M KCl, 0.008M $Na_2HPO_4$, 0.001M $KH_2PO_4$, pH 7.4 at room temperature, 0.05% Tween-20) and blocked for 1 to 2 hours at room temperature with 200 µl/well TNCNT (which is 0.5% BSA, 20mM Tris, pH 7.5 at room temperature, 120 mM NaCl, 0.2% $NAN_3$, 2mM $CaCl_2$, 0.05% Tween 20, 0.5% BSA [Calbiochem RIA grade or better]) on a plate shaker. The plates are again washed three times with PBS/Tween and then 50 µl of sample in TNCNT is added. The mixture is incubated for 15 minutes at room temperature on a plate shaker. The stock solution of purified GP $II_bIII_a$ receptor from human platelets, (0.4–1.0 mg/ml GP $II_bIII_a$ in 0.1% Triton X-100, 1 mM $CaCl_2$, 20 mM Tris, 150 mM NaCl, 0.05% $NaN_3$ in 0.3M N-acetyl glucosamine pH 7.5, stored at –70° C.), is reconstituted to about 40 µg/ml in TNCNT. Fifty µl of this diluted GP $II_bIII_a$ is then added to each well and incubated on a plate shaker at room temperature. After one hour, the plates are washed four times with PBS/Tween and 100 µl of a polyclonal or monoclonal antibody specific for GP IIIa such as AP3 (1 µg/ml) (See e.g. Newman et al., *Blood*, 65:227–232 [1985]) in ELISA buffer (PBS, 0.5% BSA, 0.05% Tween 20, 0.01% Thimerasol) is added. After a one hour incubation at room temperature on a plate shaker, the samples are washed 4 times with PBS/Tween. One hundred µl of GAM-HRP (horse radish peroxidase conjugate of goat anti-mouse IgG [Pel-Freeze Cat. 715305-1] dissolved in ELISA buffer) previously diluted to 1:10,000 is then added and the samples are incubated 1 hour at room temperature on a plate shaker. The samples are then washed 4 times with PBS/Tween and 100 ml $OPD/H_2O_2$ substrate is added ($OPD/H_2O_2$ substrate: 10 mg o-phenylenediamine in 15 ml phosphate/citrate buffer, at room temperature and covered with foil; just before use, 6.25 µl of 30% $H_2O_2$ is added to give a final solution of 0.67 mg OPD/ml in 0.0125% $H_2O_2$). (The phosphate/citrate buffer consists of 16 mM Citric Acid, 50 mM $Na_2 HPO_4$, pH 5.0). The color develops within about 3 to 20 minutes and the reaction is stopped with 100 µl 1M $H_2SO_4$. The optical density at 492 nm vs 405 nm is recorded and $IC_{50}$ values are determined.

EXAMPLE 3

Human Vitronectin-Vitronectin Receptor ($\alpha_{v\beta 3}$) ELISA Assay

A. Human Vitronectin Purification

Human vitronectin (Vn) is isolated from human plasma and purified by affinity chromatography by the method of Yatohgo et. al., (*Cell Structure and Function* 13:281–292 [1988]).

B. Human Vitronectin receptor ($\alpha_{v\beta 3}$) Purification

Human vitronection receptor (VnR) is purified from human placenta by the method of Pytela et al., (*Methods Enzymol.*, 144:475 [1987]). Alternatively the $\alpha_{v\beta 3}$ receptor can be purified from some cell lines (e.g., human embryonic kidney 293 cells) transfected with DNA sequences for both the $\alpha_v$ and $\beta_3$ subunits. The subunits are purified by employing octylglucoside extraction followed by Con-A, Heparin-Sepharose, and S-300 Chromatography.

C. Monoclonal Antibodies

Anti-GP $II_bIII_a$ monoclonal antibodies specific for human GP $III_a$ are prepared by the method of Newman et al. (*Blood*, 65:227–232 [1985]), or a similar procedure. This mouse Mab is specific for the $\beta_3$ subunit of the vitronectin receptor.

Rabbit Fab 2 anti-mouse Fc fragment horse radish peroxidase conjugate (anti-MuFc HRP) is obtained from Pel-Freeze (cat. no. 715305-1).

D. ELISA Assay

Maxisorp microtiter plates are coated with 2 µg/ml human vitronectin dissolved in PBS (50 ml/well) and stored overnight at 4° C. The plates are washed two times with PBS-0.05% Tween-20 (wash buffer) and blocked by incubating with about 150 µl/well of assay buffer (1%, BSA [RIA grade or better] in 50 mM Tris-HCl, 100 mM NaCl, 1 mM $MgCl_2$, $CaCl_2$, $MnCl_2$ pH 7.4) for 60 minutes. Dilutions of standards are prepared and putative inhibitors (Table 3) are dissolved in assay buffer. The blocked plates are emptied and 25 µl/well of inhibitor or standard solution is added to each well. Twenty-five µl of a 30 µg/ml solution of purified $\alpha_{v\beta 3}$ in assay buffer is pipetted into the coated plate. The final concentration of receptor in the assay well is about 15 µg/ml. The plate is incubated on a shaker for 60 minutes. Meanwhile, for each microtite plate, 6 ml buffer solution containing 1.5 µg/ml of mouse monoclonal antibody specific for $\beta_3$ is prepared. To this solution is added µl of the secondary antibody, which is anti-mouse-Fc-HRP antibody conjugate. For example, for one plate, prepare 6 ml of a 1.5

µg/ml mouse Mab solution to which is added 1 µl of anti-mouse-Fc-HRP antibody stock, (this represents a 1:6000 dilution of the antibody - HRP conjugate). This mixture is allowed to incubate during the receptor-inhibitor incubation. The assay plates are washed 4 times with PBS-Tween and 50 µl/well of the antibody mixture is then pipetted into the plate for a 60 minute incubation. The plate is washed 4 times and the color reaction is developed with 50 µl/well of 0.67 mg/ml o-phenyldiamine in PBS containing 0.012% $H_2O_2$. Alternatively, 16 mM citric acid, 50 mM $Na_2PO_4$ at pH 5.0 can be used as a substrate buffer. The reaction is stopped with 50 µl/well 1M $H_2SO_4$. The plates are read at 492-405 nm and the data analyzed by four-parameter fit.

EXAMPLE 4

GP $II_b III_a$-von Willebrand factor (vWF) ELISA Assay

A. ELISA Assay

Microtiter plates are coated with 1.0 µg/ml GP $II_b III_a$, prepared by the method of Fitzgerald et al., (*Anal. Biochem.* 151:169–177 [1985]) and allowed to incubate overnight in coat buffer. The plates are then washed three times in wash buffer (0.05% Tween 20 in PBS) and 150 µl of assay buffer is added and allowed to incubate for 1–2 hours at room temperature on plate shaker. The plates are washed three times and 50 µl of 2x inhibitor in assay buffer (Assay buffer: 0.5% BSA/50 mM Tris, 100 mM NaCl, 1.0 mM $CaCl_2$, 1.0mM $MgCl_2$, 1.0 mM $MnCl_2$; coat buffer is the same but without BSA) is added. Fifty µl of 4.0 µg/ml vWF (prepared as described by Ledford et al., *Thrombosis and Haemostasis*, 64(4): 569–575 [1990]) in assay buffer is then added and allowed to incubate for one hour at room temperature on plate-shaker. The plates are washed three times and the antibody mixture is added (1:5000 of mouse anti-vWF and 1:5000 of rabbit-anti-mouse-Fc-HRP, both commercially available) in assay buffer and incubated for 1 hour at room temperature on plate-shaker. Plates are again washed three times and 100 µl of substrate solution (10 mg OPD, 6.5 µl $H_2O_2$, 15 ml phosphate citrate buffer) is added and incubated at room temperature. The color change of OPD/$H_2O_2$ reagent is read at 492 nm with a 405 nm reference wavelength on the filter photometer.

EXAMPLE 5

In Vitro Human Platelet Aggregation Assay

Platelet aggregation assays are performed in human platelet rich plasma (PRP). Fifty milliliters of whole human blood (9 parts) is drawn on 3.6% sodium citrate (1 part) from a donor who has not taken aspirin or related medications for at least two weeks. The blood is centrifuged at 160×g for 10 minutes at 22° C. and allowed to stand for 5 minutes after which the PRP is decanted. Platelet poor plasma (PPP) is isolated from the remaining blood after centrifugation at 2000×g for 25 minutes. The platelet count of the PRP is diluted to about 300,000 platelets per microliter with PPP.

A 225 µl aliquot of PRP plus 25 µl of either a dilution of the test inhibitor sample or a control (PBS) is incubated for 5 minutes in a Chrono-log Whole Blood Aggregometer at 25° C. An aggregating agent (collagen, 1 µg/ml; U46619, 100 ng/ml; or ADP, 17 µM) is added and the transmission is recorded.

EXAMPLE 6

Human Fibronectin-Fibronectin Receptor ELISA Assay

A. Fibronectin-Fibronectin Recentor Purification

Fibronectin receptor is purified according to the procedures of Pytela et al., (*Methods Enzymol.* 144:475 [1985]). Briefly, fibronectin receptor is purified employing an Arg-Gly-Asp affinity chromatography from (100 mM) octylglucoside (OG) extracted human placenta. The OG extract is filtered over Sepharose 6B GRGDSPK column. The column is washed three times with three column volumes of Tris-buffered saline (TBS) TBS, 1 mM $CaCl_2$, and 25 mM OG. The receptor is eluted with TBS, 20 mM EDTA, and 25 mM Octyl thioglucoside, and is stored in 1 mM $CaCl_2$, 1 mM $MgCl_2$, at –80° C.

B. ELISA Assay

Microtiter plates are coated with 110 µl human fibronectin (at 2 µg/ml) in TBS. Plates are washed three times with TBS containing 0.05% Tween 20. Test inhibitors are then added after washing in 10 microliter aliquots. The fibronectin receptor is added in 2-fold serial dilutions with TBS containing 20 mM octyl glucoside and 2 mM $MnCl_2$. Plates are incubated three hours at room temperature, and washed with 200 µl TBS-Tween 20 buffer. 100 µl of affinity-purffied rabbit anti-human fibronectin receptor antibody is added to the wells and the plates are incubated two hours, washed twice with TBS-Tween and once with distilled water. Affinity-purified goat anti-rabbit IgG conjugated to horseradish peroxidase (100 µl) is added to each well followed by incubation for 60 minutes at room temperature. Plates are again washed twice with TBS-Tween and distilled water. 100 µl of substrate mixture (10 mg o-phenylenediamine in 25 ml 0.1M citrate-phosphate buffer, pH 5.0 6 µ30% $H_2O_2$) is added to the plates and allowed to develop. The development process is stopped by adding 50 µl of 4N $H_2SO_4$ to each well and read at 492/405 nM.

EXAMPLE 7

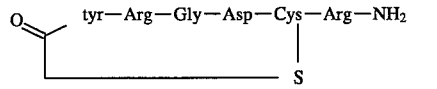

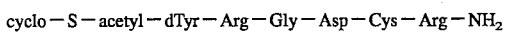

cyclo − S − acetyl − dTyr − Arg − Gly − Asp − Cys − Arg − $NH_2$

The title compound is prepared in protected form by standard solid phase peptide synthesis on 2% cross-linked para methylbenzhydryl amine polystyrene resin (Merrifield resin). The peptide is prepared by sequential addition of suitably protected amino acid residues from the resin bound arginine to the d-tyrosine residue. After the amino protecting group of the d-tyrosine residue has been removed, bromoacetic acid is coupled with diisopropylcarbodiimide. Treatment of the resin bound intermediate with liquid hydrogen fluoride induces concomitant cleavage of the protecting groups from the title compound as well as cleavage of the peptide from the resin. The crude peptide is dissolved in deionized water (1 mg/ml) and the pH of the solution is adjusted to 8.0–8.5 with ammonium hydroxide to effect cyclization. After stirring for 4 hr at ambient temperature the reaction solution is acidified to pH 3.0–3.5 with trifluoroacetic acid and then lyophilized. The resulting crude cyclic product is purified by reverse phase high performance liquid chromatography (HPLC) using a 4.6 mm×250 mm column containing 10 micron, 300 Angstrom pore size C-18 packing. The elution of the column is with an acetontrile/0.1% aqueous trifluoroacetic acid gradient going from 0 % –40% acetonitrile linearly over 80 minutes. The title compound elutes at 19 minutes. FAB mass spectrum: calc. 807.2; obs. 808.3 (M+1).

Except for compound 1, the following compounds were prepared by analogous procedures.

| Compound No. | Sequence | |
|---|---|---|
| 1 | cyclo-S-acetyl-dTyr—Arg—Gly—Asp—Cys—Arg—NH₂ | |
| 2 | cyclo-S-acetyl-dTyr—Arg—Gly—Asp—Cys—dArg—NH₂ | |
| 3 | cyclo-S-acetyl-dTyr—Arg—Gly—Asp—Cys—Lys—NH₂ | |
| 4 | cyclo-S-acetyl-dTyr—Arg—Gly—Asp—Cys—dLys—NH₂ | |
| 5 | cyclo-S-acetyl-dTyr—Arg—Gly—Asp—Cys—Orn—NH₂ | |
| 6 | cyclo-S-acetyl-dTyr—Arg—Gly—Asp—Cys—dOrn—NH₂ | |
| 7 | cyclo-S-acetyl-dTyr—Arg—Gly—Asp—Cys—Tyr—Arg—NH₂ | |
| 16 | cyclo-S-acetyl-dTyr—Lys—Gly—Asp—Pen—Arg—NH₂ | |
| 17 | cyclo-S-acetyl-dTyr—Lys—Gly—Asp—Pen—Lys—NH₂ | |
| 24 | cyclo-S-acetyl-dTyr—Arg—Gly—Asp—Cys—Arg—OH | |
| 25 | cyclo-S-acetyl-dTyr—Arg—Gly—Asp—Cys—Lys—OH | |
| 26 | cyclo-S-acetyl-dTyr—Lys—Gly—Asp—Pen—Arg—OH | |
| 27 | cyclo-S-acetyl-dTyr—Arg—Gly—Asp—Cys—Gln—NH₂ | |
| 28 | cyclo-S-(1-5)-dTyr—Arg—Gly—Asp—Cys—X | (X = aminovaleric acid) |
| 29 | cyclo-S-(1-5)-dTyr—Arg—Gly—Asp—Cys—X | (X = aminovaleric amide) |
| 30 | cyclo-S-acetyl-Tyr—Arg—Gly—Asp—Cys—Arg—NH₂ | |
| 31 | cyclo-S-acetyl-dTyr—Arg—Gly—Asp—Cys—Arg—NH₂ | Sulfoxide (isomer 1) |
| 32 | cyclo-S-acetyl-dTyr—Arg—Gly—Asp—Cys—Arg—NH₂ | Sulfoxide (isomer 2) |
| 33 | cyclo-S-acetyl-dTyr—Arg—Gly—Asp—Cys—dArg—NH₂ | Sulfoxide (isomer 1) |
| 34 | cyclo-S-acetyl-dTyr—Arg—Gly—Asp—Cys—dArg—NH₂ | Sulfoxide (isomer 2) |
| 35 | cyclo-S-acetyl-dTyr—Arg—Gly—Asp—Cys—Lys—NH₂ | Sulfoxide (isomer 1) |
| 36 | cyclo-S-acetyl-dTyr—Arg—Gly—Asp—Cys—Lys—NH₂ | Sulfoxide (isomer 2) |
| 37 | cyclo-S-acetyl-dTyr—Arg—Gly—Asp—Cys—dLys—NH₂ | Sulfoxide (isomer 1) |
| 38 | cyclo-S-acetyl-dTyr—Arg—Gly—Asp—Cys—dLys—NH₂ | Sulfoxide (isomer 2) |
| 39 | cyclo-S-acetyl-dTyr-Arg—Gly—Asp—Cys—Orn—NH₂ | Sulfoxide (isomer 1) |
| 40 | cyclo-S-acetyl-dTyr—Arg—Gly—Asp—Cys—Orn—NH₂ | Sulfoxide (isomer 2) |
| 41 | cyclo-S-acetyl-dTyr—Arg—Gly—Asp—Cys—dOrn—NH₂ | Sulfoxide (isomer 1) |
| 42 | cyclo-S-acetyl-dTyr—Arg—Gly—Asp—Cys—dOrn—NH₂ | Sulfoxide (isomer 2) |
| 43 | cyclo-S-acetyl-dTyr—Arg—Gly—Asp—Cys—Tyr—Arg—NH₂ | Sulfoxide (isomer 1) |
| 44 | cyclo-S-acetyl-dTyr—Arg—Gly—Asp—Cys—Tyr—Arg—NH₂ | Sulfoxide (isomer 2) |
| 45 | cyclo-S-phenylacetyl-dTyr—Lys—Gly—Asp—Cys—OH | |
| 46 | cyclo-S-acetyl-dTyr—Arg—Gly—Asp—Cys—OH | |
| 47 | cyclo-S-acetyl-dTyr—Arg—Gly—Asp—Pen—OH | |

EXAMPLE 8

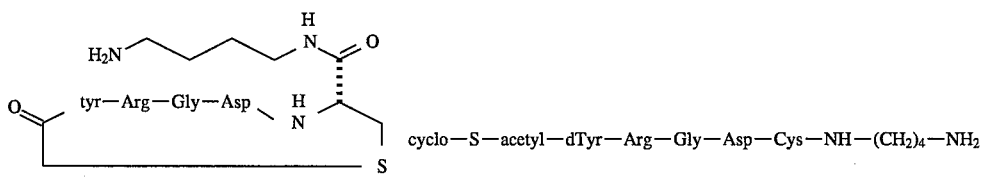

The title compound is prepared in protected form by standard solid phase peptide synthesis. Hydroxymethyl methyl polystyrene is treated with 20% phosgene in toluene for one hour. The resin is then washed six times with toluene. Excess 1,4 diaminobutane is added in toluene and mixed with the resin for 2 hours. The resin is washed with toluene followed by dimethylacetamide. The protected cysteine residue is coupled to the amine on the resin with diisopropylcabodiimide. Standard solid phase techniques are used for the addition of the subsequent amino acids. After the amino protecting group of the d-Tyrosine residue has been removed bromoacetic acid is coupled with diisopropylcarbodiimide. Treatment of the resin bound intermediate with liquid hydrogen fluoride induces concomitant cleavage of the protecting groups from the title compound as well as cleavage of the peptide from the resin. The crude peptide is dissolved in deionized water (1 mg/ml) and the pH of the solution is adjusted to 8.0–8.5 with ammonium hydroxide. After stirring for 4 hr at ambient temperature the reaction solution is acidified to pH 3.0–3.5 with trifluoroacetic acid and then lyophilized. The resulting crude cyclic product is purified by reverse phase high performance liquid chromatography (HPLC) using a 4.6 mm×250 mm column containing 10 micron, 300 Angstrom pore size C-18 packing. The elution of the column is with an acetontrile/0.1% aqueous trifluoroacetic acid gradient going from 0% –40% acetonitrile linearly over 80 minutes. The title compound elutes at 18 minutes. FAB mass spectrum: calc. 722.2; obs. 723.2(M+1).

Except for compound 12, the following compounds were prepared by analogous procedures:

| Compound No. | Sequence | |
|---|---|---|
| 12 | cyclo-S-acetyl-dTyr—Arg—Gly—Asp—Cys—NH—X | (X = butylamine) |
| 13 | cyclo-S-acetyl-dTyr—Arg—Gly—Asp—Cys—NH—X | (X = pentylamine) |
| 14 | cyclo-S-acetyl-dTyr—Arg—Gly—Asp—Cys—NH—X | (X = hexyl amine) |
| 15 | cyclo-S-acetyl-dTyr—Lys—Gly—Asp—Cys—NH—X | (X = butyl amine) |

| Compound No. | Sequence | |
|---|---|---|
| 18 | cyclo-S-acetyl-dTyr—Lys—Gly—Asp—Pen—NH—X | (X = butyl amine) |
| 22 | cyclo-S-acetyl-dTyr—Arg—Gly—Asp—Cys—NH—X | (X = propyl amine) |
| 23 | cyclo-S-acetyl-dTyr—Arg—Gly—Asp—Cys—NH—X | (X = ethyl amine) |

EXAMPLE 9

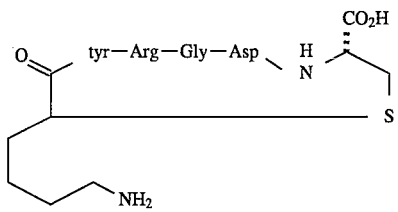

cyclo — S — 2(6-aminocaproyl)dTyr — Arg — Gly — Asp — Cys — OH

The title compound is prepared in protected form by standard solid phase peptide synthesis on 2% cross-linked polystyrene resin (Merrifield resin). After removal of the t-butyloxycarbonyl group from the d-tyrosine residue and subsequent neutralization, the 2-bromo 6-( 2-chlorobenzyloxycarbonyl) aminocaproic acid, synthesized from ε-( 2-chloro-CBZ)-L-lysine, was coupled using diisopropylcarbodiimide. Treatment of the resin bound intermediate with liquid hydrogen fluoride induces concomitant cleavage of the protecting groups from the title compound as well as cleavage of the peptide from the resin. The crude peptide is dissolved in deionized water (1 mg/ml) and the pH of the solution is adjusted to 8.0–8.5 with ammonium hydroxide. After stirring for 4 hr at ambient temperature the reaction solution is acidified to pH 3.0–3.5 with trifluoroacetic acid and then lyophilized. The resulting crude cyclic product is purified by reverse phase high performance liquid chromatography (HPLC) using a 4.6 mm×250 mm column containing 10 micron, 300 Angstrom pore size C-18 packing. The elution of the column is with an acetontrile/0.1% aqueous trifluoroacetic acid gradient going from 0% –40% acetonitrile linearly over 80 minutes. The title compound elutes at 14 minutes. FAB mass spectrum: calc. 723.2; obs. 724.2 (M+1).

Except for compounds 10 and 11, the following compounds were prepared by analogous procedures:

The title compound is prepared in protected form by standard solid phase peptide synthesis on 2% cross-linked para methylbenzhydryl amine polystyrene resin (Merrifield resin). The amino adipic add residue is incorporated as the N-Boc-δ-allyl-α-aminoadipic acid derivative. After deprotection and neutralization at the d-tyrosine residue the allyl group is removed and the peptide is cyclized with BOP. Treatment of the resin bound intermediate with liquid hydrogen fluoride induces concomitant cleavage of the protecting groups from the title compound as well as cleavage of the peptide from the resin. The resulting crude cyclic product is purified by reverse phase high performance liquid chromatography (HPLC) using a 4.6 mm×250 mm column containing 10 micron, 300 Angstrom pore size C-18 packing. The elution of the column is with an acetonitrile/0.1% aqueous trifluoroacetic acid gradient going from 0% –40% acetonitrile linearly over 80 minutes. The title compound elutes at 14 minutes. FAB mass spectrum: calc. 789.3; obs. 790.3 (M+1).

Except for compound 19, the following compounds were prepared by analogous procedures:

| Compound No. | Sequence | |
|---|---|---|
| 8 | cyclo-S-2-L-(5-guanidinovaleryl)-dTyr—Arg—Gly—Asp—Cys—OH | |
| 9 | cyclo-S-2-D-(5-guanidinovaleryl)-dTyr—Arg—Gly—Asp—Cys—OH | |
| 10 | cyclo-S-2-L-(6-aminocaproyl)-Lys—dTyr—Arg—Gly—Asp—Cys—OH | (isomer 1) |
| 11 | cyclo-S-2-L-(6-aminocaproyl)-Lys—dTyr—Arg—Gly—Asp—Cys—OH | (isomer 2) |

EXAMPLE 10

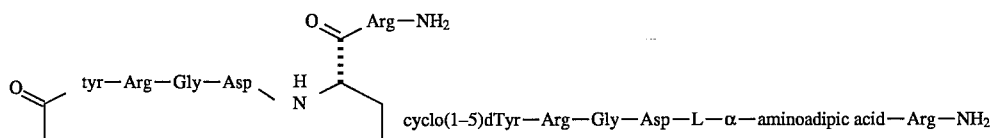

cyclo(1–5)dTyr—Arg—Gly—Asp—L—α—aminoadipic acid—Arg—NH₂

| Compound No. | Sequence |
|---|---|
| 19 | cyclo(1-5)dTyr—Arg—Gly—Asp—L-α-aminoadipic acid-Arg—NH$_2$ |
| 20 | cyclo(1-5)dTyr—Arg—Gly—Asp—L-α-aminoadipic acid-Lys—NH$_2$ |
| 21 | cyclo(1-5)dTyr—Arg—Gly—Asp—L-α-aminoadipic-butylamine |

EXAMPLE 11

Bleeding Time and EX-VIVO Platelet Aggregation - Dog Model

A. Animal preparation

Beagle dogs were premedicated with atropine (3 mg subcutaneously) and anesthetized with intravenous sodium pentobarbital solution (65 mg/ml, to effect, induction and maintenance). The dogs were placed in dorsal recumbency on heating pads, intubated, and placed on oxygen-room air mixture (free breathing). A pulse oximeter was attached and heart rate and oxygen saturation monitored. An indwelling catheter was placed in one cephalic vein through which normal saline drip (for patency) and maintenance anesthetic doses were administered, and in one saphenous vein through which test or control compound was bolused or infused.

At each proscribed time point a 5 ml whole blood sample was withdrawn via jugular venipuncture for ex vivo platelet aggregation and complete blood cell count. Manual pressure was applied to the venipuncture site following blood withdrawal to minimize hematoma formation.

At one "pre" time point, 14 ml of blood was withdrawn in order to conduct in vitro dose-response experiments.

At several timepoints bleeding times were measured. The forearm of the dog was closely shaven. A Surgicutt® automatic bleeding time device was employed to make an approximate 1 cm clean incision through the skin. Blood was blotted with the edge of a Whatman's #4 filter paper every 15 seconds. Bleeding time was measured as the time from incision to the last time blood was absorbed by the filter paper.

B. Handling of blood samples

Approximately one ml of blood withdrawn at each timepoint was placed on EDTA (purple-top vacutainer) and used to measure the complete blood cell count on a Cell-Dyne 1500 automated hematology analyzer. 3.6 ml of blood withdrawn at each timepoint was placed on a 3.8% sodium citrate (1 part to 9 parts blood) and centrifuged at 12,000 rpm for 4 seconds in an Eppendorf microcentrifuge. The resultant platelet rich plasma (PRP) was pipetted off for use in ex vivo aggregation procedures.

C. Ex Vivo olatelet aggregation

Platelet aggregation was measured in a Payton dual-channel aggregometer. The equipment was calibrated with PRP assigned as 0% light transmission and PPP as 100% light transmission. PRP was allowed to rest at room temperature for 20 minutes following separation from whole blood. 300 ml PRP was incubated at 37° C. in the aggregometer for approximately 5 minutes with the chart recorder on to establish a baseline. 10 ml ADP (1 mM) was added to the PRP and the aggregation response (change in light transmission) recorded. An aliquot of the PRP was used to perform a platelet count on the Cell-Dyne 1500 automated hematology analyzer.

D. Results

Example 7, Compound 1 (7/1)
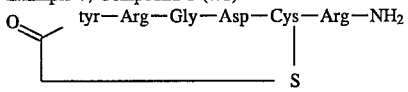

Example 7, Compound 3 (7/3)
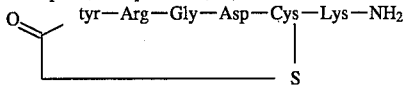

Example 7, Compound 5 (7/5)
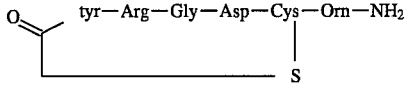

Example 7, Compound 46 (7/46)
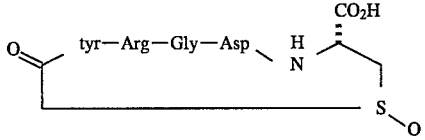

Example 7, Compound 1

Compared to 7/46, 7/1 was equipotent at inhibiting human platelet aggregation in vitro. The effect on platelet aggregation in the dog of 7/46, i.e., a bolus of 125 µg/kg plus an infusion of 3 µg/kg/min gave 100% inhibition of ex vivo aggregation throughout the infusion period. At this dose, 7/46 prolonged bleeding time to >30 minutes during the infusion. With 7/1, bleeding time was increased from pre-infusion value of 3 minutes to a mean of 6.25 minutes during the infusion. This effect is no different to that seen with a normal saline infusion.

Example 7, Compound 3

At a dose of 300 µg/kg bolus plus an infusion of 7.2 µg/kg/min this peptide inhibited ex vivo aggregation >95% without prolongation of the bleeding time. Based on potency in vitro, this was a dose equivalent to 75 µg/kg bolus plus an infusion of 2 µg/kg/min for compound D which gave a prolongation of bleeding.

Example 7, Compound 5

At a dose of 200 µg/kg bolus plus an infusion of 4.8 µg/kg/min. gave >90% inhibition of aggregation with minimal prolongation of bleeding.

EXAMPLE 12
In Vivo and In Vitro Assay Results For Platelet Aggregation Inhibitors

| Compound[1] Ex (#)/ Cpd. (#) | Sequence[2] | ELISA IC$_{50}$nM Fibrinogen[3] GPII$_b$III$_a$ | Vitronectin[4] VnR | GPII$_b$III$_a$[5] vWF | Fibronectin[6] FnR | Human[7] Platelet Aggregation IC$_{50}$nM | Rabbit[8] BT Ratio (% P.A. Inhibition) |
|---|---|---|---|---|---|---|---|
| 7/1 | 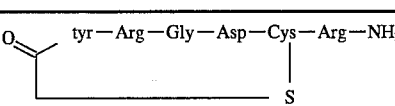 tyr—Arg—Gly—Asp—Cys—Arg—NH$_2$ | 10 | 49 | 13.8 | 57 | 83 | 1.7 (100) |
| 7/2 | 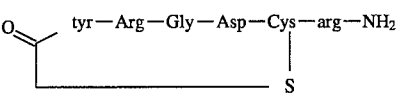 tyr—Arg—Gly—Asp—Cys—arg—NH$_2$ | 13.5 | 22 | 2.93 | 42 | | |
| 7/3 | 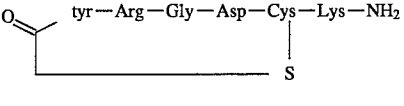 tyr—Arg—Gly—Asp—Cys—Lys—NH$_2$ | 17 | 60 | 15.9 | 201 | 320 | 1.95 (97) |
| 7/4 | 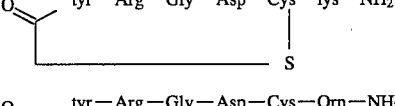 tyr—Arg—Gly—Asp—Cys—lys—NH$_2$ | 8.3 | 17 | 1.56 | 66 | | |
| 7/5 | 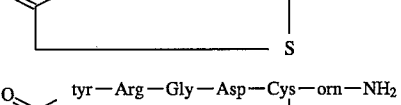 tyr—Arg—Gly—Asp—Cys—Orn—NH$_2$ | 11 | 45 | 6.84 | 63 | | 1.26 (100) |
| 7/6 | 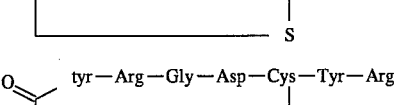 tyr—Arg—Gly—Asp—Cys—orn—NH$_2$ | 10.5 | 55 | 1.92 | 161 | 1,176 | |
| 7/7 | 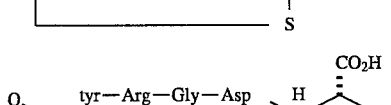 tyr—Arg—Gly—Asp—Cys—Tyr—Arg—NH$_2$ | 8.9 | 51 | | 27 | | 4.10 (98) |
| 9/8 | 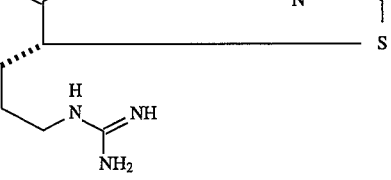 | 8.4 | 7 | 2.45 | 216 | 790 | |
| 9/9 | 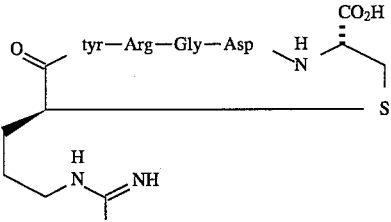 | 50 | 17 | 13.8 | 273 | 6,300 | |
| 9/10 | 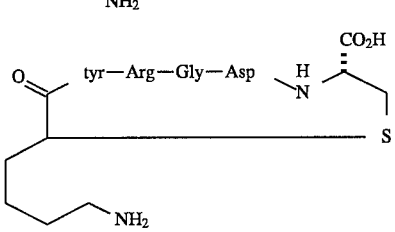 | 5.3 | 9.6 | 0.785 | 2 | 498 | 8.17 (100) |

EXAMPLE 12
In Vivo and In Vitro Assay Results For Platelet Aggregation Inhibitors
| Compound[1] Ex (#)/ Cpd. (#) | Sequence[2] | ELISA IC$_{50}$nM | | | | Human[7] Platelet Aggregation IC$_{50}$nM | Rabbit[8] BT Ratio (% P.A. Inhibition) |
|---|---|---|---|---|---|---|---|
| | | Fibrinogen[3] GPII$_b$III$_a$ | Vitronectin[4] VnR | GPII$_b$III$_a$[5] vWF | Fibronectin[6] FnR | | |
| 9/11 | 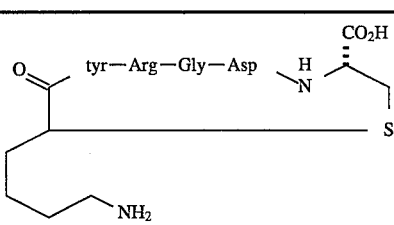 | 14.3 | 11.2 | 6.95 | 160 | 3,177 | |
| 8/12 | 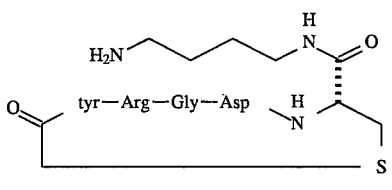 | 10 | 70 | 5.40 | | 390 | 0.94 (96) |
| 8/13 | 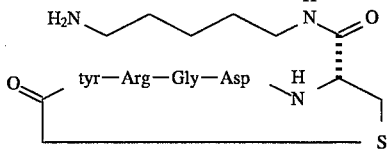 | 9 | 32 | 5.30 | 473 | 590 | 1.13 (98) |
| 8/14 | 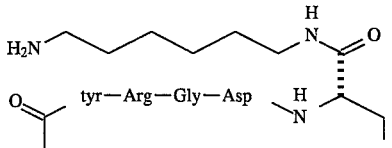 | | | | | | |
| 8/15 | 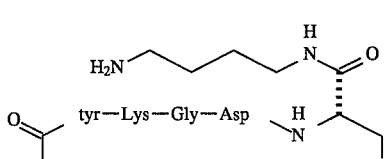 | | | | | | |
| 7/16 | 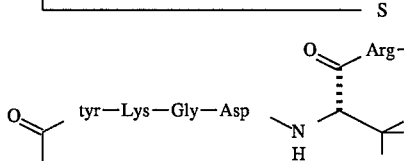 | 150 | 120,000 | 53.5 | >10,000 | 506 | |
| 7/17 | 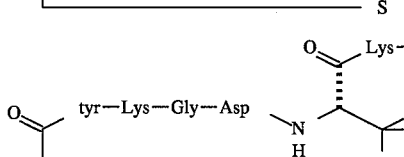 | 238 | 100,000 | 73.1 | >10,000 | | 1.13 (100) 1.0 (100) |
| 8/18 | 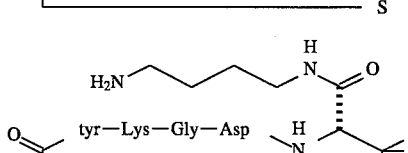 | | | | | | |

EXAMPLE 12
In Vivo and In Vitro Assay Results For Platelet Aggregation Inhibitors -continued
| Compound[1] Ex (#)/ Cpd. (#) | Sequence[2] | ELISA IC$_{50}$nM | | | | Human[7] Platelet Aggregation IC$_{50}$nM | Rabbit[8] BT Ratio (% P.A. Inhibition) |
|---|---|---|---|---|---|---|---|
| | | Fibrinogen[3] GPII$_b$III$_a$ | Vitronectin[4] VnR | GPII$_b$III$_a$[5] vWF | Fibronectin[6] FnR | | |
| 10/19 | 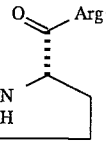 | 8.9 | 32 | 2.90 | 745 | 180 205 | |
| 10/20 | 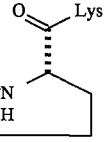 | 12.4 | 20 | 2.74 | 2,310 | 183 | 2.0 (100) |
| 10/21 | 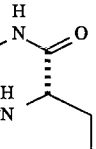 | | | | | | |
| 8/22 | 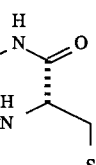 | 15 | 36 | 4.73 | 176 | 387 | 1.27 (99) |
| 8/23 | 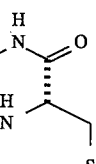 | 14 | 35 | 4.67 | 61 | 470 | 0.81 (88) |
| 7/24 |  | | | | | | |
| 7/25 |  | | | | | 370 | |
| 7/26 | 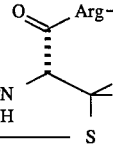 | | | | | | |
| 7/27 |  | 3.1 | 49 | | | 1760 | 0.77 (72) 0.93 (99) |

EXAMPLE 12
In Vivo and In Vitro Assay Results For Platelet Aggregation Inhibitors

| Compound[1] Ex (#)/ Cpd. (#) | Sequence[2] | ELISA IC$_{50}$nM | | | | Human[7] Platelet Aggregation IC$_{50}$nM | Rabbit[8] BT Ratio (% P.A. Inhibition) |
|---|---|---|---|---|---|---|---|
| | | Fibrinogen[3] GPII$_b$III$_a$ | Vitronectin[4] VnR | GPII$_b$III$_a$[5] vWF | Fibronectin[6] FnR | | |
| 7/28 | HO—(structure with tyr—Arg—Gly—Asp and S) | 70 | 650 | | | 52,200 | |
| 7/29 | H$_2$N—(structure with tyr—Arg—Gly—Asp and S) | | | | | | |
| 7/30 | Tyr—Arg—Gly—Asp—Cys—Arg—NH$_2$ (with S) | | | | | | |
| 7/31 | tyr—Arg—Gly—Asp—Cys—Arg—NH$_2$ (with S–O) | 9.5 | 39 | 2.04 | 330 | 230 | |
| 7/32 | tyr—Arg—Gly—Asp—Cys—Arg—NH$_2$ (with S–O) | 55 | 82 | 59.3 | 386 | 750 | 1.17 (99) |
| 7/33 | tyr—Arg—Gly—Asp—Cys—arg—NH$_2$ (with S–O) | 6.8 | 22 | 0.994 | 470 | 500 | |
| 7/34 | tyr—Arg—Gly—Asp—Cys—arg—NH$_2$ (with S–O) | 48 | 57 | 33.6 | 409 | 4,900 | 0.94 (64) |
| 7/35 | tyr—Arg—Gly—Asp—Cys—Lys—NH$_2$ (with S–O) 3-bromyl tyrosine | 16.5 | 27 | 6.11 | 1,070 | | |
| 7/36 | tyr—Arg—Gly—Asp—Cys—Lys—NH$_2$ (with S–O) 3-bromyl tyrosine | 108 | 78 | 45.6 | 524 | | 0.77 (91) |
| 7/37 | tyr—Arg—Gly—Asp—Cys—lys—NH$_2$ (with S–O) 3-bromyl tyrosine | 6.3 | 38 | 1.82 | 994 | | |

EXAMPLE 12
In Vivo and In Vitro Assay Results For Platelet Aggregation Inhibitors

| Compound[1] Ex (#)/ Cpd. (#) | Sequence[2] | ELISA IC$_{50}$nM | | | | Human[7] Platelet Aggregation IC$_{50}$nM | Rabbit[8] BT Ratio (% P.A. Inhibition) |
| --- | --- | --- | --- | --- | --- | --- | --- |
| | | Fibrinogen[3] GPII$_b$III$_a$ | Vitronectin[4] VnR | GPII$_b$III$_a$[5] vWF | Fibronectin[6] FnR | | |
| 7/38 | tyr—Arg—Gly—Asp—Cys—lys—NH$_2$ (cyclic, S-acyl); 3-bromyl tyrosine | 69 | 65 | 47.3 | 615 | | |
| 7/39 | tyr—Arg—Gly—Asp—Cys—Orn—NH$_2$ (cyclic, S-acyl) | 5.3 | 64 | | 3.27 | 93 | |
| 7/40 | tyr—Arg—Gly—Asp—Cys—Orn—NH$_2$ (cyclic, S-acyl) | 43 | 300 | | 67.7 | 1,950 | 1.09 (71) |
| 7/41 | tyr—Arg—Gly—Asp—Cys—orn—NH$_2$ (cyclic, S-acyl) | 5.3 | 42 | | 1.21 | 340 | 1.50 (98) |
| 7/42 | tyr—Arg—Gly—Asp—Cys—orn—NH$_2$ (cyclic, S-acyl) | 23 | 153 | | 42.1 | 6,680 | 1.14 (41) |
| 7/43 | tyr—Arg—Gly—Asp—Cys—Tyr—Arg—NH$_2$ (cyclic, S-acyl) | | | | | 350 | |
| 7/44 | tyr—Arg—Gly—Asp—Cys—Tyr—Arg—NH$_2$ (cyclic, S-acyl) | 94 | 160 | | 60.3 | 8,470 | 1.18 (52) |
| 7/45 | tyr—Lys—Gly—Asp + phenyl-CH(S-)–C(=O)–NH–CH(CO$_2$H)– (cyclic) | >20,000 | 1 | >10,000 | | 220 | 4.47 (94) |
| 7/46 | tyr—Arg—Gly—Asp—NH–CH(CO$_2$H)–CH$_2$–S (cyclic, S-acyl) | 3.2 | 5 | 0.18 | 3,390 | 150 | 8.77 (99) 2.74 (55) |
| 7/47 | tyr—Lys—Gly—Asp—NH–CH(CO$_2$H)–C(CH$_3$)$_2$–S (cyclic, S-acyl) | 4.2 | >20,000 | 10.3 | >10,000 | 486 | 8.57 (96) |

[1]The numerical designation refers to the example and compound number in that example where the method of synthesis is described.
[2]The three letter code used in this table refers to the naturally occurring α-amino acid residues unless the code begins with a lower case letter in which case it represents the unnatural α-amino acid. Two formats for depicting the structures of the cyclic peptides are used in this table. When the residue Cys is connected to the letter "S", it represents a thioether linkage where "S" is the sulfur from Cys.

EXAMPLE 12
In Vivo and In Vitro Assay Results For Platelet Aggregation Inhibitors

| Compound[1] Ex (#)/ Cpd. (#) | Sequence[2] | ELISA IC$_{50}$nM | | | | Human[7] Platelet Aggregation IC$_{50}$nM | Rabbit[8] BT Ratio (% P.A. Inhibition) |
|---|---|---|---|---|---|---|---|
| | | Fibrinogen[3] GPII$_b$III$_a$ | Vitronectin[4] VnR | GPII$_b$III$_a$[5] vWF | Fibronectin[6] FnR | | |

[3]This assay was conducted as described in Example 2.
[4]This assay was conducted as described in Example 3.
[5]This assay was conducted as described in Example 4.
[6]This assay was conducted as described in Example 6.
[7]This assay was conducted as described in Example 5.
[8]This assay was conducted as described in Example 1. BT Ratio is the bleeding time ratio pre-administration/post-administration. % P.A. inhibition is the percent ex vivo platelet aggregation inhibition in the rabbit.

---

What is claimed is:

1. A peptide having an $IC_{50}$ in a human platelet aggregation inhibition assay of no more than at least about 3 μM, represented by a sequence selected from the group consisting of:

$Xaa_1$-Arg-Gly-Asp-$Xaa_2$, and
$Xaa_1$-Lys-Gly-Asp-$Xaa_2$
where;

$Xaa_1$ is a single amino acid selected from;
  Gly,
  D-Ala,
  D-Val,
  D-Leu,
  D-lie,
  D-Phe,
  D-Tyr, and
  D-Pro $Xaa_2$ represents an α-amino acid bonded to $Xaa_1$ selected from Cys and Pen, and where a positively charged nitrogen containing exocyclic moiety is bonded to $Xaa_2$ through a functional group of $Xaa_2$, wherein the positively charged exocyclic moiety is a D or L α-amino acid selected from;
  His,
  Lys,
  Arg, and
  Orn, wherein the α-carboxyl group of the D or L α-amino acid is optionally derivatized with an amino or lower alkyl substituted amino group.

2. The peptide of claim 1 wherein the linkage bonding $Xaa_1$ and $Xaa_2$ is selected from thioether and sulfoxide.

3. The peptide of claim 2 wherein the linkage further comprises an acetyl group wherein the β-carbon of the acetyl group is bonded to the sulfur and wherein the carbonyl forms an amide with the α-amino of $Xaa_1$.

4. A peptide selected from the group:
cyclo-S-acetyl-dTyr-Arg-Gly-Asp-Cys-Arg-$NH_2$; cyclo-S-acetyl-dTyr-Arg-Gly-Asp-Cys-dArg-$NH_2$; cyclo-S-acetyl-dTyr-Arg-Gly-Asp-Cys-L ys-$NH_2$; cyclo-S-acetyl-dTyr-Arg-Gly-Asp-Cys-dLys-$NH_2$; cyclo-S-acetyl-dTyr-Arg-Gly-Asp-Cys-Orn-$NH_2$; cyclo-S-acetyl-dTyr-Arg-Gly-Asp-Cys-dOrn-$NH_2$; cyclo-S-acetyl-dTyr-Arg-Gly-Asp-Cys-Tyr-Arg-$NH_2$; cyclo-S-acetyl-dTyr-Arg-Gly-Asp-Cys-NH-X (X=butylamine); cyclo-S-acetyl-dTyr-Arg-Gly-Asp-Cys-NH-X (X=pentylamine); cyclo-S-acetyl-dTyr-Arg-Gly-Asp-Cys-NH-X (X=hexylamine); cyclo-S-acetyl-dTyr-Lys-Gly-Asp-Cys-NH-X (X=butylamine); cyclo-S-acetyl-dTyr-Lys-Gly-Asp-Pen-NH-X (X=butylamine); cyclo(1–5)dTyr-Arg-Gly-Asp-L-α-aminoadipic acid-Arg-$NH_2$; cyclo(1–5)dTyr-Arg-Gly-Asp-L-α-aminoadipic acid-Lys-$NH_2$; cyclo( 1–5)dTyr-Arg-Gly-Asp-L-α-aminoadipic-butylamine; cyclo-S-acetyl-dTyr-Arg-Gly-Asp-Cys-NH-X (X=propylamine); cyclo-S-acetyl-dTyr-Arg-Gly-Asp-Cys-NH-X (X-ethylamine); cyclo-S-acetyl-dTyr-Lys-Gly-Asp-Pen-Arg-$NH_2$; cyclo-S-acetyl-dTyr-Lys-Gly-Asp-Pen-Lys-$NH_2$; cyclo-S-acetyl-dTyr-Arg-Gly-Asp-Cys-Arg-OH; cyclo-S-acetyl-dTyr-Arg-Gly-Asp-Cys-Lys-OH; cyclo-S-acetyl-dTyr-Lys-Gly-Asp-Pen-Arg-OH; cyclo-S-acetyl-dTyr-Arg-Gly-Asp-Cys-Gln-$NH_2$; cyclo-S-acetyl-Tyr-Arg-Gly-Asp-Cys-Arg-$NH_2$; cyclo-S-acetyl-dTyr-Arg-Gly-Asp-Cys-Arg-$NH_2$ Sulfoxide (isomer 1); cyclo-S-acetyl-dTyr-Arg-Gly-Asp-Cys-Arg-$NH_2$ Sulfoxide (isomer 2); cyclo-S-acetyl-dTyr-Arg-Gly-Asp-Cys-dArg-$NH_2$ Sulfoxide (isomer 1); cyclo-S-acetyl-dTyr-Arg-Gly-Asp-Cys-dArg-$NH_2$ Sulfoxide (isomer 2); cyclo-S-acetyl-dTyr-Arg-Gly-Asp-Cys-Lys-$NH_2$ Sulfoxide (isomer 1); cyclo-S-acetyl-dTyr-Arg-Gly-Asp-Cys-Lys-$NH_2$ Sulfoxide (isomer 2); cyclo-S-acetyl-dTyr-Arg-Gly-Asp-Cys-dLys-$NH_2$ Sulfoxide (isomer 1); cyclo-S-acetyl-dTyr-Arg-Gly-Asp-Cys-dLys-$NH_2$ Sulfoxide (isomer 2); cyclo-S-acetyl-dTyr-Arg-Gly-Asp-Cys-Orn-$NH_2$ Sulfoxide (isomer 1); cyclo-S-acetyl-dTyr-Arg-Gly-Asp-Cys-Orn-$NH_2$ Sulfoxide (isomer 2); cyclo-S-acetyl-dTyr-Arg-Gly-Asp-Cys-dOrn-$NH_2$ Sulfoxide (isomer 1); cyclo-S-acetyl-dTyr-Arg-Gly-Asp-Cys-dOrn-$NH_2$ Sulfoxide (isomer 2); cyclo-S-acetyl-dTyr-Arg-Gly-Asp-Cys-Tyr-Arg-$NH_2$ Sulfoxide (isomer 1); and cyclo-S-acetyl-dTyr-Arg-Gly-Asp-Cys-Tyr-Arg-$NH_2$ (Sulfoxide (isomer 2).

* * * * *